(12) United States Patent
Harrow et al.

(10) Patent No.: US 12,150,857 B2
(45) Date of Patent: Nov. 26, 2024

(54) MULTI-COMPONENT LOCKING IMPLANT

(71) Applicant: Mako Surgical Corp., Weston, FL (US)

(72) Inventors: Matthew Ervin Harrow, Mooresville, NC (US); Amit Mistry, Weston, FL (US)

(73) Assignee: Mako Surgical Corp., Weston, FL (US)

( * ) Notice: Subject to any disclaimer, the term of this patent is extended or adjusted under 35 U.S.C. 154(b) by 357 days.

(21) Appl. No.: 17/517,059

(22) Filed: Nov. 2, 2021

(65) Prior Publication Data

US 2022/0133479 A1 May 5, 2022

Related U.S. Application Data

(60) Provisional application No. 63/196,928, filed on Jun. 4, 2021, provisional application No. 63/109,104, filed on Nov. 3, 2020.

(51) Int. Cl.
| | |
|---|---|
| *A61F 2/28* | (2006.01) |
| *A61B 17/56* | (2006.01) |
| *A61F 2/30* | (2006.01) |
| *A61F 2/46* | (2006.01) |

(52) U.S. Cl.
CPC .......... *A61F 2/28* (2013.01); *A61B 2017/564* (2013.01); *A61F 2002/2839* (2013.01); *A61F 2002/30112* (2013.01); *A61F 2002/30383* (2013.01); *A61F 2002/30387* (2013.01); *A61F 2002/4633* (2013.01)

(58) Field of Classification Search
CPC ...... A61F 2/30; A61F 2/28; A61F 2/42; A61F 2/4202; A61F 2/30734
See application file for complete search history.

(56) References Cited

U.S. PATENT DOCUMENTS

| | | | |
|---|---|---|---|
| 4,743,262 | A | 5/1988 | Tronzo |
| 5,598,005 | A | 1/1997 | Wang et al. |
| 5,824,084 | A | 10/1998 | Muschler |
| 6,112,109 | A | 8/2000 | D'Urso |
| 6,319,712 | B1 | 11/2001 | Meenen et al. |
| 6,475,243 | B1 | 11/2002 | Sheldon et al. |
| 6,613,092 | B1 | 9/2003 | Kana et al. |
| 6,711,432 | B1 | 3/2004 | Krause et al. |
| 6,723,131 | B2 | 4/2004 | Muschler |

(Continued)

FOREIGN PATENT DOCUMENTS

| | | |
|---|---|---|
| WO | 2014145406 A1 | 9/2014 |
| WO | 2019104392 A1 | 6/2019 |

OTHER PUBLICATIONS

Extended European Search Report including Written Opinion for Application No. 21205871.3 dated Mar. 23, 2022, pp. 1-10.

*Primary Examiner* — Christopher J Beccia
(74) *Attorney, Agent, or Firm* — Lerner David LLP

(57) ABSTRACT

A method for treating a bone includes cutting away a portion of the bone, including cutting non-planar features into the bone for engagement by implant components. The method further includes fitting the multiple implant components to the bone, with at least some of the multiple implant components engaging the non-planar features cut into the bone. The implant components interlock such that later added implant components secure earlier added implant components in place on the bone.

16 Claims, 30 Drawing Sheets

(56) References Cited

U.S. PATENT DOCUMENTS

| | | |
|---|---|---|
| 7,641,672 B2 | 1/2010 | Fallin et al. |
| 7,747,311 B2 | 6/2010 | Quaid, III |
| 7,831,292 B2 | 11/2010 | Quaid et al. |
| 8,095,200 B2 | 1/2012 | Quaid, III |
| 8,183,042 B2 | 5/2012 | Liao et al. |
| 8,287,522 B2 | 10/2012 | Moses et al. |
| 8,391,954 B2 | 3/2013 | Quaid, III |
| 8,483,863 B1 | 7/2013 | Knox |
| 8,551,178 B2 | 10/2013 | Sharkey et al. |
| 8,617,171 B2 | 12/2013 | Park et al. |
| 8,652,148 B2 | 2/2014 | Zuhars |
| 8,657,482 B2 | 2/2014 | Malackowski et al. |
| 8,845,736 B2 | 9/2014 | Zhang et al. |
| 8,911,499 B2 | 12/2014 | Quaid et al. |
| 9,002,426 B2 | 4/2015 | Quaid et al. |
| 9,039,998 B2 | 5/2015 | Guillemot et al. |
| 9,056,017 B2 | 6/2015 | Kotlus |
| 9,060,794 B2 | 6/2015 | Kang et al. |
| 9,278,001 B2 | 3/2016 | Forsell |
| 9,486,321 B1 | 11/2016 | Smith et al. |
| 9,492,237 B2 | 11/2016 | Kang et al. |
| 9,636,185 B2 | 5/2017 | Quaid et al. |
| 9,724,165 B2 | 8/2017 | Arata et al. |
| 9,757,242 B2 | 9/2017 | Dong et al. |
| 9,757,243 B2 | 9/2017 | Jones et al. |
| 9,775,681 B2 | 10/2017 | Quaid et al. |
| 9,775,682 B2 | 10/2017 | Quaid et al. |
| 9,820,861 B2 | 11/2017 | Smith |
| 10,028,789 B2 | 7/2018 | Quaid et al. |
| 10,085,804 B2 | 10/2018 | Nortman et al. |
| 10,231,790 B2 | 3/2019 | Quaid et al. |
| 10,433,921 B2 | 10/2019 | Librot |
| 11,154,370 B2 | 10/2021 | Librot |
| 2003/0135216 A1* | 7/2003 | Sevrain ................. A61B 90/92 606/328 |
| 2004/0193268 A1 | 9/2004 | Hazebrouck |
| 2005/0272153 A1 | 12/2005 | Xuenong et al. |
| 2006/0142657 A1 | 6/2006 | Quaid et al. |
| 2007/0142751 A1 | 6/2007 | Kang et al. |
| 2007/0173815 A1 | 7/2007 | Murase |
| 2007/0265705 A1 | 11/2007 | Gaissmaier et al. |
| 2007/0270685 A1 | 11/2007 | Kang et al. |
| 2008/0004633 A1 | 1/2008 | Arata et al. |
| 2008/0010705 A1 | 1/2008 | Quaid et al. |
| 2008/0010706 A1 | 1/2008 | Moses et al. |
| 2009/0000626 A1 | 1/2009 | Quaid et al. |
| 2009/0000627 A1 | 1/2009 | Quaid et al. |
| 2009/0012531 A1 | 1/2009 | Quaid et al. |
| 2009/0012532 A1 | 1/2009 | Quaid et al. |
| 2009/0306499 A1 | 12/2009 | Van Vorhis et al. |
| 2009/0314925 A1 | 12/2009 | Van Vorhis et al. |
| 2010/0016467 A1 | 1/2010 | Truckai et al. |
| 2010/0217400 A1 | 8/2010 | Nortman et al. |
| 2010/0256504 A1 | 10/2010 | Moreau-Gaudry et al. |
| 2010/0256692 A1 | 10/2010 | Kang et al. |
| 2011/0172611 A1 | 7/2011 | Yoo et al. |
| 2012/0109152 A1 | 5/2012 | Quaid, III |
| 2013/0053648 A1 | 2/2013 | Abovitz et al. |
| 2013/0060278 A1 | 3/2013 | Bozung et al. |
| 2013/0144392 A1 | 6/2013 | Hughes |
| 2013/0211523 A1 | 8/2013 | Southard et al. |
| 2014/0180290 A1 | 6/2014 | Otto et al. |
| 2014/0188134 A1 | 7/2014 | Nortman et al. |
| 2014/0194887 A1 | 7/2014 | Shenoy |
| 2014/0263214 A1 | 9/2014 | Dahotre et al. |
| 2014/0371897 A1 | 12/2014 | Lin et al. |
| 2015/0182295 A1 | 7/2015 | Bozung et al. |
| 2016/0338782 A1 | 11/2016 | Bowling et al. |
| 2017/0007406 A1 | 1/2017 | Cui et al. |
| 2017/0020613 A1 | 1/2017 | Kang et al. |
| 2017/0151021 A1 | 6/2017 | Quaid, III |
| 2017/0181755 A1 | 6/2017 | Librot |
| 2017/0333137 A1 | 11/2017 | Roessler |
| 2017/0333138 A1 | 11/2017 | Arata et al. |
| 2017/0340389 A1 | 11/2017 | Otto et al. |
| 2018/0168749 A1 | 6/2018 | Dozeman |
| 2018/0168750 A1 | 6/2018 | Staunton et al. |
| 2019/0015164 A1 | 1/2019 | Quaid et al. |
| 2019/0029764 A1 | 1/2019 | Nortman et al. |
| 2019/0374295 A1 | 12/2019 | Librot |
| 2020/0046412 A1* | 2/2020 | Nachtrab ............... A61F 2/4202 |
| 2020/0060843 A1 | 2/2020 | Evans et al. |
| 2021/0369361 A1 | 12/2021 | Librot |

\* cited by examiner

MULTI-COMPONENT LOCKING IMPLANT

CROSS-REFERENCE TO RELATED APPLICATIONS

The present application claims the benefit of the filing date of U.S. Provisional Application No. 63/109,104, filed Nov. 3, 2020, and U.S. Provisional Application No. 63/196,928, filed Jun. 4, 2021, the disclosures of which are incorporated herein by reference.

BACKGROUND

Treatment for a human bone in a diseased or injured state can include removing the affected portion of the bone and replacing the removed bone with a functionally similar implant. Removal of tumors, for example, may require irregular shaped cuts in order to minimize the damage to healthy bone. In some cases it may be preferred to cut the majority of the bone from one general direction instead of making a secondary or beyond cuts through different entry points into the bone to fully release the affected area with the least amount of healthy bone loss.

Known implants are typically unitary in construction, and must be secured to the bone by fasteners, such as bone screws, and/or adhesives, such as bone cement. Fastening an implant to a bone requires careful alignment of the fastener to the implant after the implant is in place. Further, insertion of the fasteners displaces remaining healthy bone and increases the number of separate foreign objects that must be introduced to the patient. Other known implants, in order to reduce or avoid the need for fasteners, extend deep into the cancellous bone and, in some cases, engage the cortical bone from the inside. Such implants also displace healthy bone, and necessitate removal of even more bone if a revision is performed.

BRIEF SUMMARY

In an aspect of the present disclosure, a portion of the bone to be removed may be identified in patient specific data. The patient specific data may be used to plan cuts for removing the portion of bone. Interlocking implant components may also be designed for functionally replacing the portion of bone to be removed. In addition to removing the identified portion of bone, the cuts may be planned to create multiple ports or slots in remaining cortical bone for retaining corresponding protrusions of the implant components. The slots may specifically be negative non-planar features, and the protrusions may be corresponding positive non-planar features.

The implant components may include mating faces with interlocking features to prevent separation of the implant components after they have been fitted to the bone. The interlocking features may be, for example, complementary holes and posts. These features could be interlocked with deformable press fit or snap fit features similar to those used in plastic component assemblies. The implant components may therefore be individually freely insertable and removable from their intended position on the post-operative bone, but may interlock with one another in such a way that the implant components retain each other to the bone when they have all been implanted with few or no traditional screw type fasteners between the bone and the implant.

According to another aspect, a method for treating a bone may comprise cutting away a portion of the bone, including the creation of multiple pathways for implant insertion in the remaining cortical bone. The method may further include fitting multiple implant components to the bone to replace the cut away portion of the bone, including passing at least one protrusion of each of the implant components into a respective one of the pathways, at least one of the implant components being applied to the bone along a first direction and at least one of the implant components being applied to the bone along a second direction transverse to the first direction. The implant components may be any combination of metal, plastic, bioabsorbable implant material, allo- or auto-grafts, or any other bone filler material.

In some arrangements according to any of the foregoing, the step of cutting away the portion of the bone may include removing a region of bone under an intended post-operative location of a concave portion of a completed implant provided by the implant components in combination. The step of fitting multiple implant components to the bone may include locking at least one earlier fitted implant component into position on the bone by placing at least one later fitted implant component at an intended post-operative location of the at least one later fitted implant component relative to the bone.

In some arrangements according to any of the foregoing, fitting the multiple implant components to the bone may include engagement of interlocking features between neighboring implant components. Interlocking features between neighboring implant components may include corresponding concavities and convexities. The interlocking features of a component may extend in a direction transverse to the direction along which the component is fitted to the bone, so engaging additional components to the interlocking features may prevent the component from backing out of the bone. Interlocking additional implants will add to the degrees of freedom of the fixation.

In some arrangements according to any of the foregoing, each of the implant components may be fitted to the bone along a different direction than any other of the implant components. Two or more implants could be inserted from one direction and their position could be locked with an additional implant being inserted from another direction.

In some arrangements according to any of the foregoing, the method may include fitting four implant components to the bone.

In some arrangements according to any of the foregoing, the method may include, before cutting the bone, using patient specific data to identify the portion of the bone to be removed, including locating a target region of the bone and planning placement of the pathways to stably retain a prosthesis for functionally replacing the portion of bone to be removed.

In some arrangements according to any of the foregoing, the method may include designing the implant components such that the implant components can functionally replace the portion of the bone to be removed when fitted to the bone.

In some arrangements according to any of the foregoing, the pathways may be negative non-planar features, and the protrusions are positive non-planar features.

In another aspect, a method for treating a bone may comprise resecting the bone, fitting a first implant component to a first section of the resected bone along a first direction, fitting a second implant component to a second section of the bone along a second direction transverse to the first direction, and engaging the second implant component to the first implant component.

In some arrangements according to any of the foregoing, engaging the second implant component to the second implant component may include insertion of posts extending from a mating face of the second implant component into holes in a mating face of the first implant component while fitting either or both of the first implant component and the second implant component to the bone.

In some arrangements according to any of the foregoing, the posts may each have a jagged profile to inhibit removal of the posts from the holes.

In some arrangements according to any of the foregoing, fitting the first implant and the second implant into the bone may include slotting a protrusion of each of the first implant and the second implant into a respective pathway cut into cortical bone.

In some arrangements according to any of the foregoing, the protrusions may be positive non-planar features, and the pathway may be negative non-planar features.

In some arrangements according to any of the foregoing, the implant components may be fabricated according to a plan derived from patient specific data.

In some arrangements according to any of the foregoing, the first implant component and the second implant component may cooperate to provide a continuous prosthetic bone surface after being fitted to the bone.

In some arrangements according to any of the foregoing, the method may further comprise fitting a third implant component to the bone along a third direction transverse or at a non-zero angle relative to the first and second directions. The method may yet further comprise fitting a fourth implant component to the bone along a fourth direction transverse or at a non-zero angle relative to the first, second, and third directions. The third and fourth implant components may cooperate with the first and implant components to provide the continuous prosthetic bone surface after being fitted to the bone.

In some arrangements according to any of the foregoing, fitting the first, second, third, and fourth implant components to the bone includes engaging each respective implant component to two neighboring implant components.

In some arrangements according to any of the foregoing, engaging the second implant component to the first implant component may include disposing a portion of the second implant component through an aperture of the first implant component.

In some arrangements according to any of the foregoing, at least one of the pathways may be curved.

In some arrangements according to any of the foregoing, one of the implant components may include a channel extending along a surface thereof and is configured to engage with the bone such that the channel aligns with one of the pathways, and wherein another of the implant components is configured to simultaneously engage both the channel and the one of the pathways.

In some arrangements according to any of the foregoing, the step of cutting away a portion of the bone may include removing the cut away portion of the bone and separating the remaining bone into two remaining bone portions. The method may comprise the further steps of distracting the two remaining bone portions, and, while the two remaining bone portions are distracted, disposing an implant component between the two bone portions.

In some arrangements according to any of the foregoing, the method may include securing a selected one of the implant components to the bone by disposing a pair of pins through the selected one of the implant components and into the bone such that the pair of pins engage one another within the bone.

In another aspect, a method for treating bone may comprise cutting away and removing a portion of a bone such that the bone is separated into two remaining bone portions, and rejoining the two remaining bone portions with a patient-specific implant component.

In some arrangements according to any of the foregoing, the method may comprise securing the implant component to a first one of the remaining bone portions by disposing a pair of pins through the implant component and into the first one of the remaining bone portions such that the pair of pins engages one another within the first one of the remaining bone portions.

In some arrangements according to any of the foregoing, the pair of pins may be a first pair of pins, and the method may further comprise securing the implant component to a second one of the remaining bone portions by disposing a second pair of pins through the implant component and into the second one of the remaining bone portions such that the second pair of pins engages one another within the second one of the remaining bone portions.

In some arrangements according to any of the foregoing, the first pair of pins may include a first receiving pin including a neck portion and a first receiving pin having two arms spaced to receive and grip the neck, and the second pair of pins may include a second receiving pin including a hole extending therethrough and a second gripping pin including two arms spaced to press against an interior of the hole of the second receiving pin when received therein. In various examples, the first and second pair of pins may be the only pins, or there may be additional pins. Such additional pins may be in further pairs or may interlock with the first and/or second pairs of pins.

In some arrangements according to any of the foregoing, the method may comprise distracting the two remaining bone portions before disposing the implant component between the two remaining bone portions.

In some arrangements according to any of the foregoing, the implant component may be a first implant component. The method may comprise reducing the two remaining bone portions as to engage the first implant component with the two remaining bone portions, and fitting a second implant component onto the two remaining bone portions and the first implant component.

In some arrangements according to any of the foregoing, the step of fitting the second implant component onto the two remaining bone portions and the first implant component may include guiding an engaging feature of the second implant component along a curved path.

In some arrangements according to any of the foregoing, the engaging feature of the second implant component may be an arcuate rib.

In some arrangements according to any of the foregoing, the curved path may be defined at least partially by a bone channel defined in one of the two remaining bone portions and at least partially by an implant channel defined in the first implant component, and wherein the first implant component is positioned such that the bone channel is aligned with the implant channel during the step of fitting the second implant component.

In another aspect, an implant system may comprise a first implant component constructed according to a patient-specific design including at least one bone-facing surface shaped to conform to a first resected surface produced by a planned cut to a bone and at least one external surface shaped to recreate part of an exterior contour of a portion of the bone to be removed by the planned cut. The system may also comprise a second implant component including a first portion receivable within the implant component and a second portion configured to extend into the bone when the bone-facing surface is conformed to the first resected surface and the first portion is received within the implant component, the second implant component being constructed according to a patient-specific design including at least one second bone-facing surface shaped conform to a second resected surface produced by a planned cut to the bone and at least one second external surface shaped to recreate part of an exterior contour of the portion of bone to be removed.

In some arrangements according to any of the foregoing, the first and second portions of the second implant component may be portions of an arcuate rib.

In some arrangements according to any of the foregoing, the first implant component may include an arcuate channel, the second implant component may include a tab, and the second implant component may be rotatable relative to the first implant component while the rib is received within the channel to a position wherein the tab abuts the first implant component.

In some arrangements according to any of the foregoing, the first implant component may define a first channel and the second implant component may define a second channel. The first and second channels may be located such that the first implant component and second implant component may be placed into mutual abutment to form a body having a hole extending therethrough provided by the first and second channels, and further comprising a pin having an external shape matching an internal shape of the hole.

In some arrangements according to any of the foregoing, the internal shape of the hole may be a numeral 8 on one cross-section.

In some arrangements according to any of the foregoing, the second implant component may include a tab extending over the second channel.

In another aspect, a bone implant assembly may comprise a first component including a first positive non-planar feature and a first mating face, wherein holes in the first mating face extend into the first component, and a second component including a second positive non-planar feature, a second mating face, and posts extending from the second mating face at a spacing corresponding to the locations of the holes in the first mating face.

In some arrangements according to any of the foregoing, the implant assembly of may comprise a third component including a third positive non-planar feature, posts, and holes, and a fourth component including a fourth positive non-planar feature, posts, and holes. The first component may include posts extending from a surface other than the first mating face, and the second component may include holes extending into the second component from a surface other than the second mating face.

In some arrangements according to any of the foregoing, the first, second, third, and fourth implant components may be fabricated according to a design derived from patient specific data to retain each other to a bone without fasteners.

DETAILED DESCRIPTION

Figure 1:
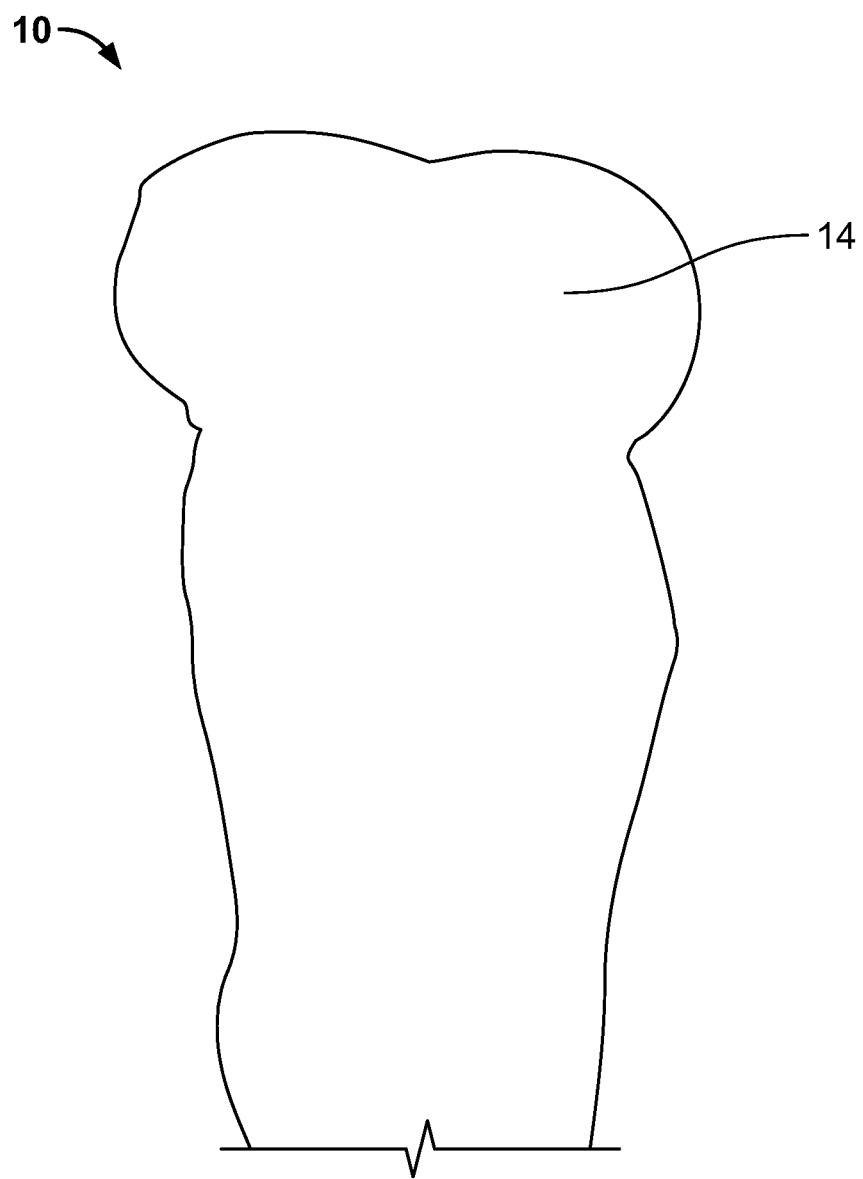
FIG. 1 is an illustration of an exemplary pre-operative bone.

An exemplary bone 10 is shown in a pre-operative state in FIG. 1. In the pre-operative state, bone 10 includes a target region 14. As used herein, the terms "target region" or "target portion" refer to a portion of bone planned to be removed for any reason, such as, for example, any kind of defect in the bone, including those resulting from disease states or acute trauma. For example, target region 14 may be a portion of bone 10 including a cancerous tumor. Target region 14 includes condyles in the illustrated example, but the procedure described herein could be used to treat any portion of a bone. Planning of cutting boundaries to remove a cancerous tumor or any other bone defect may be, for example, according to any of the methods and processes described in U.S. patent application Ser. No. 17/201,479, filed Mar. 15, 2021, the entirety of which is hereby incorporated herein by reference. Such processes, or cutting plans derived from such processes, may be modified to provide holes, channels, dovetailing features, or other features in the bone for interface with or fastening of any of the implants as described throughout this disclosure.

Figure 2:
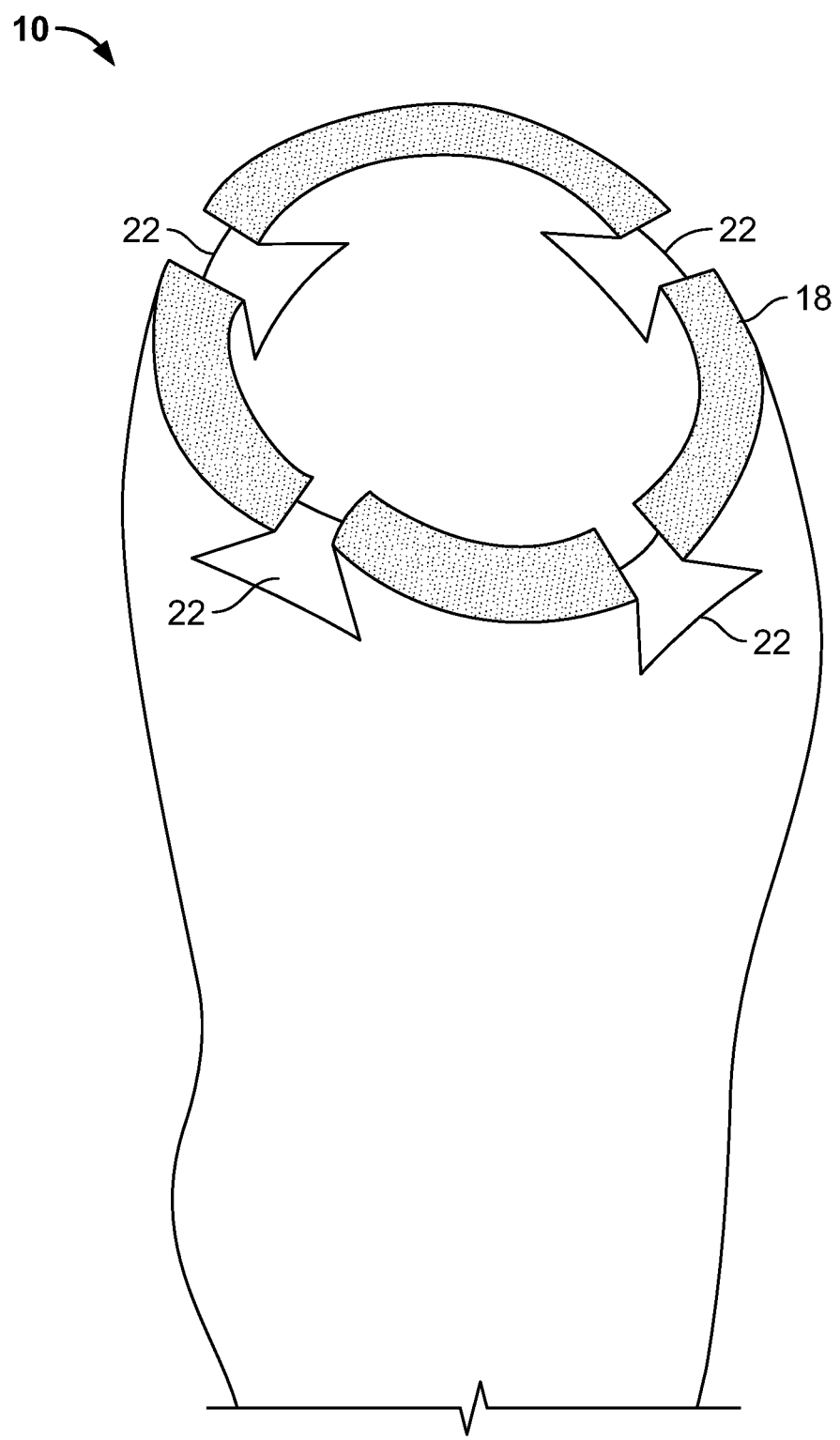
FIG. 2 is an illustration of the bone of FIG. 1 in a resected state.

Bone 10 is shown in a resected state in FIG. 2. In the resected state, target region 14 of bone 10 has been removed. Cutting away target region 14 leaves a rim 18 on the cortical bone at an end of the remaining bone 10. Negative non-planar features 22 are cut deeper into the bone than rim 18.

Figure 3:
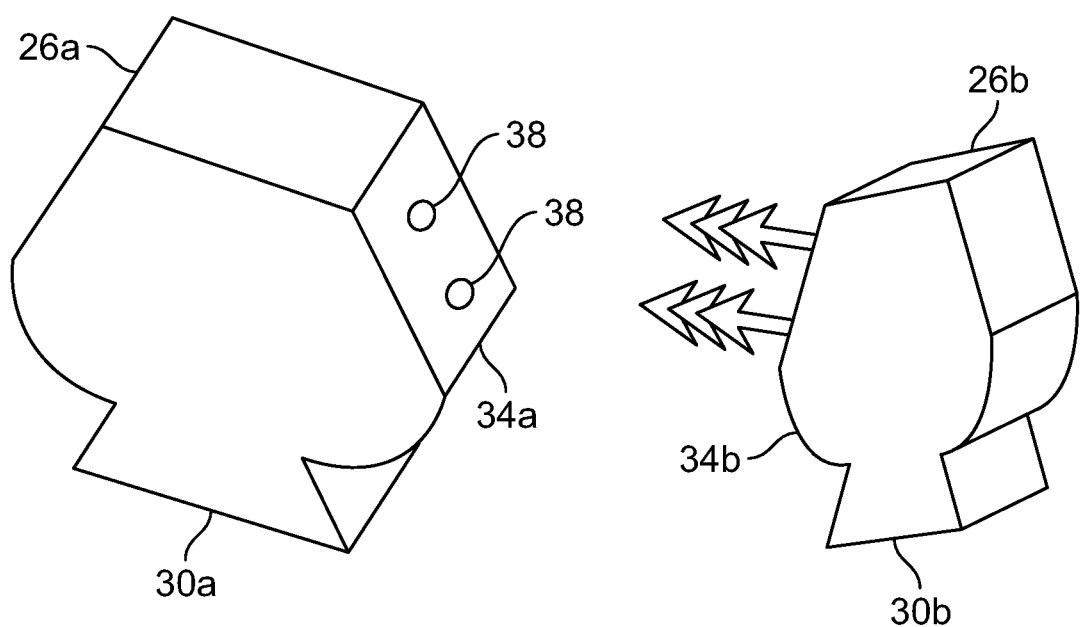
FIG. 3 is a close view of portions of two implant components for application to the bone of FIG. 1.

Cut-away portions of a first implant component 26a and a second implant component 26b are illustrated in FIG. 3. First implant component 26a and second implant component 26b include a first positive non-planar feature 30a and a second positive non-planar feature 30b, respectively. Positive non-planar features 30 are shaped to fit negative non-planar features 22 cut into the bone. Negative non-planar features 22 are shown and described as cut into the cortical bone with regard to the illustrated example, but in other arrangements the negative non-planar features 22 extend into the cancellous bone instead or in addition to the cortical bone. The positive non-planar features 30 in such arrangements would be configured to engage those negative non-planar features 22 in a similar manner despite their differing location. Regardless, the negative non-planar features 22 are pathways or channels for the insertion of implants or implant components 26a, 26b into the remaining bone 10. Both implant components 26a, 26b can both be fitted to the bone 10 by slotting the respective positive non-planar feature 30a, 30b into negative non-planar features 22.

First implant component 26a and second implant component 26b also include a first mating face 34a and a second mating face 34b (not visible from the perspective of FIG. 3), respectively. Mating faces 34 are located to press together when implant components 26 are fitted to bone 10 such that implant components 26 cooperate form a smooth exterior surface. In the illustrated example, first implant component 26a includes holes or apertures 38 extending into first implant component 26a from first mating face 34a. Second implant component 26b includes two posts 42 extending from second mating face 34b at locations corresponding to locations of holes 38 in first mating face 34a. When implant components 26 are fitted to bone 10, posts 42 pass into holes 38 to lock implant components 26 into place.

Posts 42 of the illustrated arrangement have jagged profiles to anchor posts 42 within holes 38 and prevent implant components 26 from slipping out of place after being fitted onto bone 10. In alternative arrangements, posts 42 simply have an interference fit within holes 38. In further alternative arrangements, both mating faces 34 include holes 38 and posts 42 in a complementary arrangement. Mating faces 34 can also, or in the alternative, include any known mutual retaining features, such as those disclosed in U.S. Pat. No. 6,475,243, filed Sep. 19, 2000, and U.S. Pat. No. 9,757,242, filed Mar. 11, 2013, the entireties of which are incorporated herein by reference.

Mutual retaining features on mating faces 34 between neighboring implant components 26 may include corresponding concavities and convexities of any shape. The retaining features of a first component 26a may extend in a direction transverse to the direction along which first component 26a is fitted to bone 10, so engaging additional components 26 to the retaining features would prevent first component 26 from backing out of bone 10.

Figure 4:
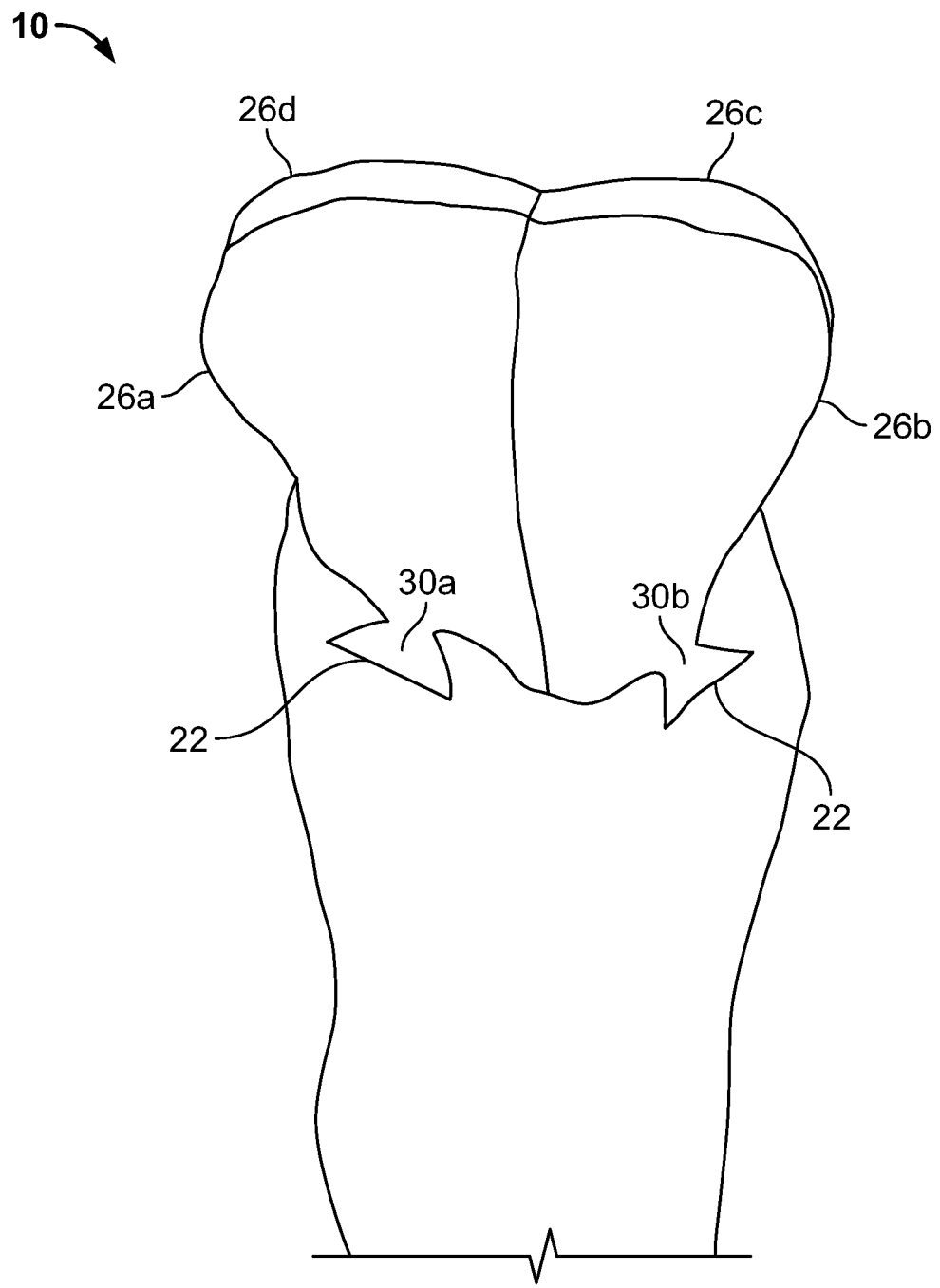
FIG. 4 is an illustration of the bone of FIG. 1 in a post-operative state.
Figure 5:
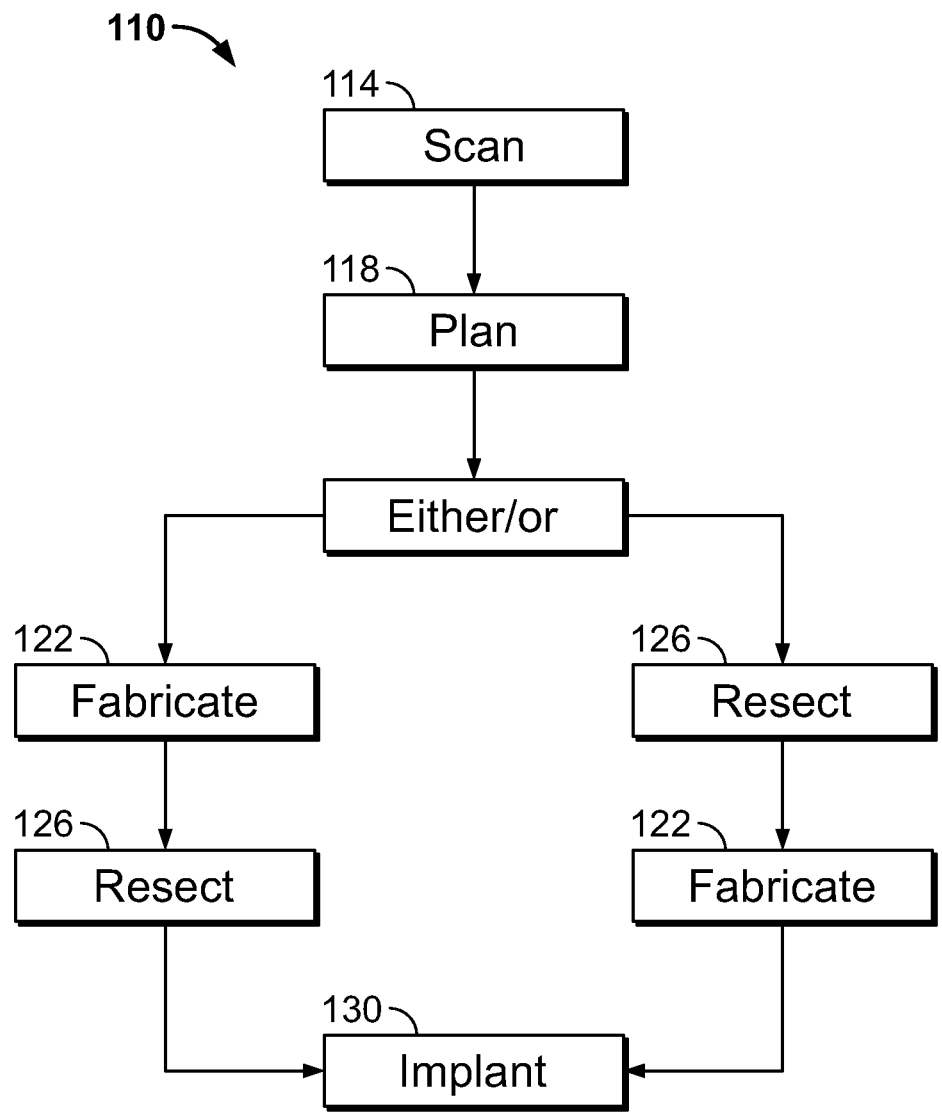
FIG. 5 is a flowchart of a surgical method according to an aspect of the disclosure.

Bone 10 is shown in a post-operative state in FIG. 4, wherein first implant component 26a and second implant component 26b, along with a third implant component 26c and a fourth implant component 26d, are fitted onto bone 10 to functionally replace an uninjured, healthy state of target region 14. Here, functional replacement or recreation refers to acting as a prosthetic replacement of a removed portion of bone 10. Implant components 26a, 26b, 26c, 26d may be constructed according to a patient-specific design to collectively form an implant body with an exterior contour that at least partially matches the pre-operative shape of bone 10. The patient-specific design may be derived from, for example, sonogram, CT scan, MRI, any other pre-operative imaging, or any other method of mapping the pre-operative shape of bone 10. Third implant component 26c and fourth implant component 26d are generally similar to first implant component 26a and first implant component 26b. Implant components 26 can therefore all be fitted to bone 10 by slotting their respective positive non-planar features into negative non-planar features 22 in the cortical bone. Fitting implant components 26 to bone 10 further includes passing posts 42 into holes 38 on respective mating faces 34, thereby anchoring adjacent implant components 26 to each other. In the illustrated example, each implant component 26 has one positive non-planar feature 30, but in various alternative arrangements, some implant components 26 have more than one positive non-planar feature 30, and in yet further alternative arrangements some implant components 26 have no positive non-planar feature 30 and instead engage only other implant components 26. In further alternatives, implant components 26 may include one or more negative non-planar features while bone 10 includes a corresponding number of positive non-planar features.

A method 110 associated with implant components 26 described above is shown in FIG. 4. Patient specific data is acquired in a scanning step 114. Scanning here refers to any technique for imaging a relevant portion of bone 10, such as computer aided tomography, ultrasound imaging, or magnetic resonance imaging. The patient specific information acquired in scanning step 114 is used in a planning step 118 to determine where to cut bone 10 and the shape and number of implant components 26 to be used. In particular, planning step 118 includes locating any target portion 14 of bone 10. As noted above, the "target portion" here is used to refer to any condition that may warrant removal of a portion of bone, including presence of a cancerous tumor or acute trauma. Method 110 is therefore applicable in both oncology and orthopedics. Planning step 118 further includes determining locations and an order for cuts to be made to bone 10 to remove target portion 14, and to place features in remaining cortical bone for engagement with implant components 26. In the illustrated example, the features are slots, specifically negative non-planar features 22 as shown in FIGS. 2 and 4. Placement of the cuts may be optimized to minimize the amount of bone to be removed while creating resection geometry capable of retaining implant components 26. Planning step 118 may further include designing implant components 26 complementary to the planned placement of the cuts to bone 10. In the example illustrated in FIGS. 1-4, components 26 are designed to include protrusions, specifically positive non-planar features 30 shown in FIGS. 3 and 4. Moreover, components 26 are designed to interlock with one another to hold themselves in an assembled arrangement upon bone 10 when positive non-planar features 30 are slotted into respective negative non-planar features 22 without use of fasteners through bone 10. However, it should be understood that the techniques described herein may also be used with fasteners through the bone where appropriate. In this example, implant components 26 are designed in a planning step 118 to effectively become a single prosthesis when interlocked and situated on bone 10 that functionally replaces target region 14. In other examples, implant components 26 may be only partially designed, or not designed at all, in pre-operative planning step 118. In such other examples, implant components 26 are instead partially or entirely designed after a resection is performed so as to allow for reference to be made to the actual post-operative geometry of the bone during the designing. Thus, according to a determination made in planning step 118 or, in some examples, before scanning step 114, planning step 118 may be followed immediately by either a fabricating step 122 or a resecting step 126.

If implant components 26 are designed in planning step 118, they are fabricated in a fabricating step 122 either before proceeding to resecting step 126 or after completion of resecting step 126. If implant components 26 are not completely designed by the end of planning step 118, fabricating step 122 follows resecting step 126 and includes generating or finalizing the design for implant components 26 with reference made to actual post-operative geometry of the bone. For examples of techniques for obtaining post-operative geometry of bone, reference may be made to U.S. Pat. No. 10,716,630, filed Jul. 13, 2017, the entirety of which is hereby incorporated herein by reference.

Fabricating step 122 can include any single process or combination of processes, including conventional or computer numerical control machining, lost wax casting, or additive manufacturing. Implant components 26 could be custom made, off the shelf, or a combination of custom made and off the shelf. Thus, some or all of the fabrication step 122 may take place far in advance of a given procedure. Further, components 26 can be made from any biocompatible material with suitable structural properties for functionally replacing target region 14. Such biocompatible materials include titanium, nitinol, and polyether ether ketone.

In a resecting step 126, which may directly follow either pre-operative planning step 118 or fabricating step 122, the cuts to bone 10 are executed as planned during planning step 118. In the illustrated example, resecting step 126 transitions bone 10 from the pre-operative state shown in FIG. 1 to the resected state shown in FIG. 2.

Finally, implant components 26 generated during fabricating step 122 are fitted to bone 10 in an implanting step 130 following resecting step 126. In implanting step 130, each positive non-planar feature 30 of implant components 26 is slotted into a respective negative non-planar feature 22 as determined during planning step 118. Each implant component 26 is fitted onto bone 10 along a unique direction that is transverse to the directions along which other implant components 26 are fitted to the bone 10. Implanting step 130 further includes pressing mating faces 34 of each implant component 26 into abutment with the corresponding mating faces 34 of neighboring implant components 26. Pressing mating faces 34 into abutment involves engaging respective features of each pair of mating faces 34 with one another. Specifically, in the illustrated example, pressing mating faces 34 of two implant components 26 into abutment includes guiding posts 42 of one of the implant components 26 into holes 38 of the other implant component 26. Either or both of posts 42 and holes 38 may include deformable features, such as elastic portions, ridges, teeth, or tabs that resiliently engage with corresponding features of the other of holes 38 and posts 42 after posts 42 are inserted into holes 38, to retain posts 42 within holes 38. Upon completion of implanting step 130, the mutual engagement of implant components 26 holds implant components 26 together on bone 10, without fasteners through bone 10, to collectively act as a prosthetic that functionally replaces target region 14 as shown in FIG. 4. Outward facing surfaces of implant components 26 cooperate to provide a continuous prosthetic bone surface.

The dovetail fit between implant components 26 and bone 10, referring to the illustration of the non-planar features as positive and negative dovetails, is presented as an example. In other arrangements, any number of implant components 26 may engage the bone with other non-planar feature features, such as such as pins or tabs that press fit into holes or slots, respectively, or interlocking serrations or teeth. In further arrangements, dovetail features of other shapes may be used to engage implant components 26 to bone 10. In various arrangements, any or all of implant components 26 may engage bone 10 in an individually releasable manner, with the interaction between implant components 26 serving to lock each of them to bone 10.

Either or both of resecting step 126 and implanting step 130 may be performed with a computer assisted surgery (CAS) system. For additional details regarding suitable CAS systems, reference can be made to U.S. Pat. No. 10,433,921, filed Dec. 19, 2016, and U.S. patent application Ser. No. 17/167,154, filed Feb. 4, 2021, the entirety of which are hereby incorporated herein by reference. For example, resecting step 126 may be executed by a motorized, computer controlled cutting tool. The computer controlled cutting tool may be guided by inputs from a surgeon throughout execution of the surgical plan or may be controlled by the CAS to execute the surgical plan without additional guidance by a surgeon. Alternatively, resecting step 126 may be executed with a customized cutting guide or with free-hand control of a cutting tool.

Figure 6:
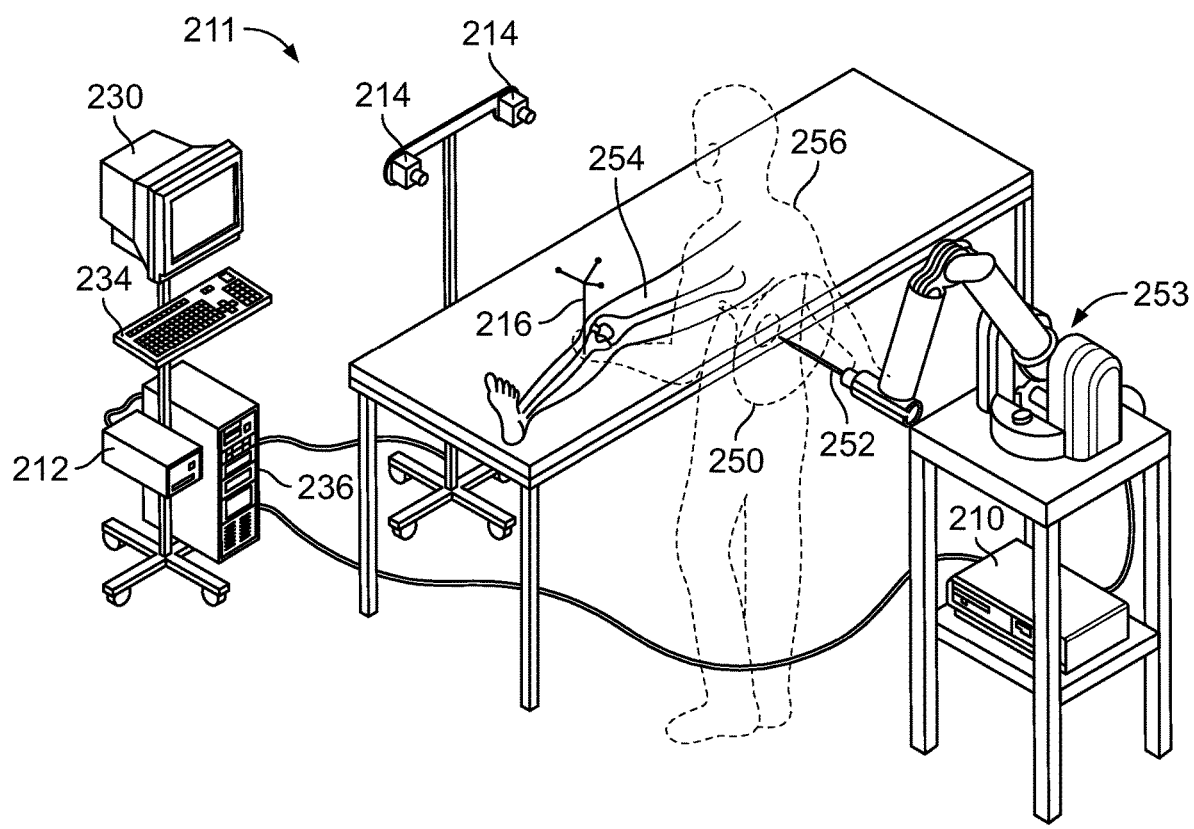
FIG. 6 is a diagrammatic illustration of an exemplary operating room in which a haptic device is used with a computer-assisted surgery system.

FIG. 6 is a diagrammatic illustration of an exemplary operating room in which a haptic device 253 is used with a CAS 211. Computer-assisted surgery system 211 may include a display device 230, an input device 234, and a processor based system 236, for example a computer. Input device 234 may be any suitable input device including, for example, a keyboard, a mouse, or a touch screen. Display device 230 may be any suitable device for displaying two-dimensional and/or three-dimensional images, for example a monitor or a projector. If desired, display device 230 may be a touch screen and be used as an input device. One example of a system incorporating a haptic device 253 is described in greater detail in U.S. Pat. No. 7,831,292, filed Jul. 16, 2003, the entirety of which is incorporated by reference herein.

Haptic device 253 is, in the illustrated example, a robotic device. Haptic device 253 may be controlled by a processor based system, for example a computer 210. Computer 210 may also include power amplification and input/output hardware. Haptic device 253 may communicate with CAS system 211 by any suitable communication mechanism, whether wired or wireless.

Also shown in FIG. 6 is a storage medium 212 may be coupled to processor based system 236. Storage medium 212 may accept a digital medium which stores software and/or other data. A surgical tool or instrument 252 is shown coupled to haptic device 253. Surgical tool 252 is preferably mechanically coupled to haptic device 253, such as by attaching or fastening it. However, if desired, surgical tool 252 may be coupled, either directly or indirectly, to haptic device 253 by any other suitable method, for example magnetically. Surgical tool 252 may be haptically controlled by a surgeon remotely or haptically controlled by a surgeon 256 present in proximity to surgical tool 252, although autonomous control with surgeon oversight is possible as well. Surgical tool 252 may be, for example, a bur, saw, laser, waterjet, cautery tool, or other trackable tool capable of cutting or otherwise shaping or resecting patent tissue, including bone. Patient tissue and bone may be referred to interchangeably herein and may include cartilage, tendons, skin tissue, and/or bone whether it be cortical or cancellous bone.

Haptic object 250 is a virtual object used to guide and/or constrain the movement and operations of surgical tool 252 to a target area inside a patient's anatomy 254, for example the patient's leg. In this example, haptic object 250 is used to aid the surgeon 256 to target and approach the intended anatomical site of the patient. Haptic feedback forces may be used to slow and/or stop the surgical tool's movement if it is detected that a portion of surgical tool 252 will intrude or cross over pre-defined boundaries of the haptic object. Furthermore, haptic feedback forces can also be used to attract (or repulse) surgical tool 252 toward (or away from) haptic object 250 and to (or away from) the target. If desired, surgeon 256 may be presented with a representation of the anatomy being operated on and/or a virtual representation of surgical tool 252 and/or haptic object 250 on display 230.

In other examples, the haptic device 253 has autonomous and/or non-haptic controls. The device 253, in various haptic and non-haptic examples, could be patient mounted, table mounted, or hand held.

CAS system 211 preferably includes a localization or tracking system that determines or tracks the position and/or orientation of various trackable objects, such as surgical instruments, tools, haptic devices, patients, donor tissue and/or the like. The tracking system may continuously determine, or track, the position of one or more trackable markers disposed on, incorporated into, or inherently a part of the trackable objects, with respect to a three-dimensional coordinate frame of reference. Markers can take several forms, including those that can be located using optical (or visual), magnetic or acoustical methods. Furthermore, at least in the case of optical or visual systems, location of an object's position may be based on intrinsic features, landmarks, shape, color, or other visual appearances, that, in effect, function as recognizable markers.

Any type of tracking system may be used, including optical, magnetic, and/or acoustic systems, which may or may not rely on markers. Many tracking systems are typically optical, functioning primarily in the infrared range. They may include a stationary stereo camera pair that is focused around the area of interest and sensitive to infrared radiation. Markers emit infrared radiation, either actively or passively. An example of an active marker is a light emitting diode ("LED"). An example of a passive marker is a reflective marker, such as ball-shaped marker with a surface that reflects incident infrared radiation. Passive systems may include an infrared radiation source to illuminate the area of focus. A magnetic system may have a stationary field generator that emits a magnetic field that is sensed by small coils integrated into the tracked tools.

With information from the tracking system on the location of the trackable markers, CAS system 211 may be programmed to be able to determine the three-dimensional coordinates of an end point or tip of a tool and, optionally, its primary axis using predefined or known (e.g. from calibration) geometrical relationships between trackable markers on the tool and the end point and/or axis of the tool. A patient, or portions of the patient's anatomy, can also be tracked by attachment of arrays of trackable markers. In the illustrated example, the localizer is an optical tracking system that comprises one or more cameras 214 that preferably track a probe 216. As shown in FIG. 6, cameras 214 may be coupled to processor based system 236. If desired, cameras 214 may be coupled to computer 210. Probe 216 may be a conventional probe. If desired, the probe may be rigidly attached to haptic device 253 or integrated into the design of haptic device 253.

In one implementation, processor based system 236 may include image guided surgery software to provide certain user functionality, e.g., retrieval of previously saved surgical information, preoperative surgical planning such as that generated in the planning step 122, determining the position of the tip and axis of instruments, registering a patient and preoperative and/or intraoperative diagnostic image datasets to the coordinate system of the tracking system, etc. Full user functionality may be enabled by providing the proper digital medium to storage medium 212 coupled to computer 236. The digital medium may include an application specific software module. The digital medium may also include descriptive information concerning the surgical tools and other accessories. The application specific software module may be used to assist a surgeon with planning and/or navigation during specific types of procedures. For example, the software module may display predefined pages or images corresponding to specific steps or stages of a surgical procedure. At a particular stage or part of a module, a surgeon may be automatically prompted to perform certain tasks or to define or enter specific data that will permit, for example, the module to determine and display appropriate placement and alignment of instrumentation or implants or provide feedback to the surgeon. Other pages may be set up to display diagnostic images for navigation and to provide certain data that is calculated by the system for feedback to the surgeon. Instead of or in addition to using visual means, the CAS system could also communicate information in other ways, including audibly (e.g. using voice synthesis) and tactilely, such as by using a haptic interface. For example, in addition to indicating visually a trajectory for a drill or saw on the screen, a CAS system may feed information back to a surgeon whether he is nearing some object or is on course with an audible sound. To further reduce the burden on the surgeon, the module may automatically detect the stage of the procedure by recognizing the instrument picked up by a surgeon and move immediately to the part of the program in which that tool is used.

The software which resides on computer 236, alone or in conjunction with the software on the digital medium, may process electronic medical diagnostic images, register the acquired images to the patient's anatomy, and/or register the acquired images to any other acquired imaging modalities, e.g., fluoroscopy to CT, MRI, etc. If desired, the image datasets may be time variant, i.e. image datasets taken at different times may be used. Media storing the software module can be sold bundled with disposable instruments specifically intended for the procedure. Thus, the software module need not be distributed with the CAS system. Furthermore, the software module can be designed to work with specific tools and implants and distributed with those tools and implants. Moreover, CAS system can be used in some procedures without the diagnostic image datasets, with only the patient being registered. Thus, the CAS system need not support the use of diagnostic images in some applications—i.e. an imageless application.

Haptic device 213, components thereof, or similar systems may be used to perform highly accurate bone resections, such as in the execution of the resection step 126.

Further arrangements of interlocking implant components may include components inserted between separated portions of a bone. For example, if a portion of a body of a long bone, such as a femur or tibia, is removed, leaving two or more separate remaining portions of the bone in the patient, the two or more remaining portions of the bone may be rejoined by an implant constructed from multiple implant components. In such arrangements, each separate remaining bone portion may be implanted with a separate CAS tracker, which may be used for positioning of the bone portions or implant components by the CAS system. In further examples, interlocking implant components may include components held to one another by further components acting as a key. Components may also be provided with integral fasteners having an interference fit with one another. Moreover, components may be used to replace a middle portion of a bone, such as portion of a femoral shaft, while leaving end portions, such as native condyles, intact.

Figure 7A:
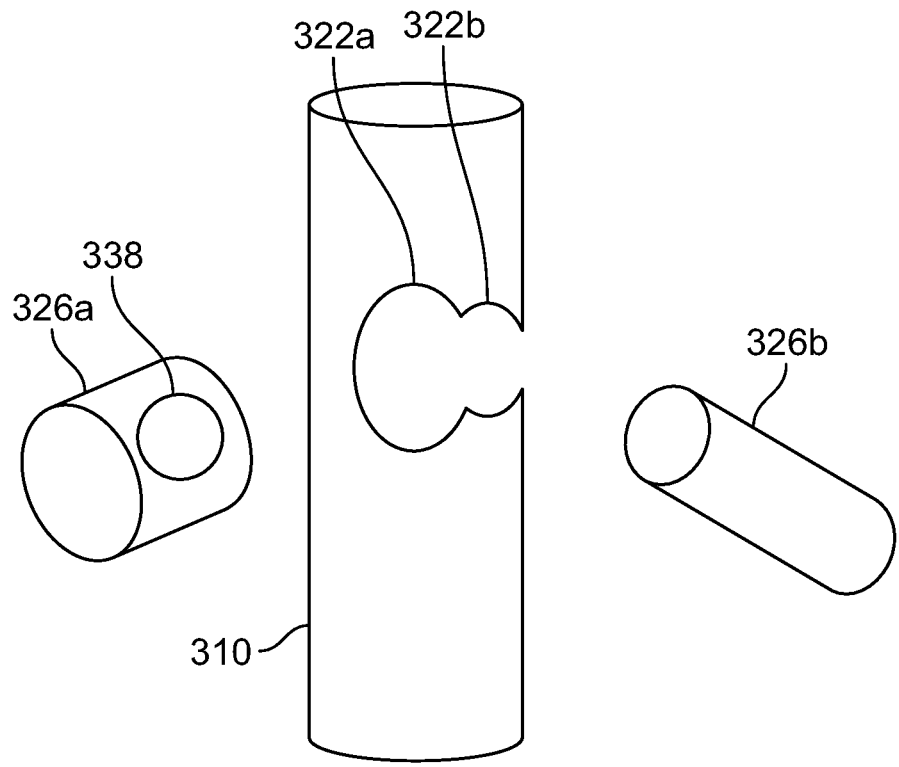
FIGS. 7A and 7B are schematic illustrations of two stages of a surgical method according to an aspect of the disclosure.
Figure 7B:
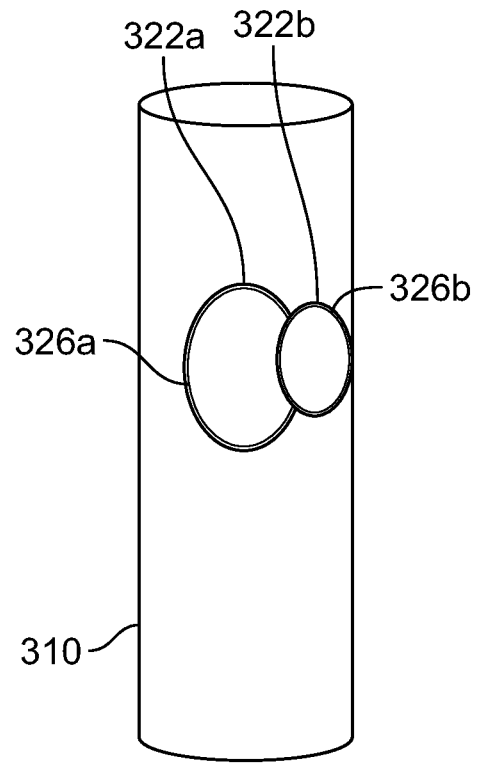

FIGS. 7A and 7B illustrate engagement between a first implant component 326a and a second implant component 326b and fitting of first implant component 326a and second implant component 326b to a bone 310 according to an example. As shown in FIG. 7A, a first channel 322a and a second channel 322b are cut into bone 310. The channels 322a, 322b of the illustrated example are cylindrical in shape, and may therefore be formed by drilling. In other examples, channels may have other shapes which may be formed, for example, by sawing, milling, or any combination of cutting processes, and may intersect an exterior surface of bone 310 at any number of places.

First channel 322a has a size and shape matching an external perimeter of first implant component 326a, and second channel 322b has a size and shape matching an external perimeter of second implant component 326b. In the illustrated example, first channel 326a overlaps second channel 326b at a surface of bone 310, but in other examples first channel 326a may be spaced from second channel 326b at the surface of bone 310, and channels 326a, 326b may intersect inside bone 310. The first implant component 326a includes an aperture 338 extending partially or entirely therethrough. In the illustrated example, aperture 338 is an enclosed channel, but in other arrangements, aperture 338 may be an open notch at the edge of first implant component 326a. Thus, first implant component 326a, after being fitted to bone 310 by insertion along a first direction into first channel 322a, may be locked to bone 310 by fitting second implant component 326b to bone 310 by inserting second implant component 326b along a second direction transverse to first direction into second channel 322b such that a portion of second implant component 326b extends into or through aperture 338 as shown in FIG. 7B. The implant components 326a, 326b in their mutual locking position form a surface flush with an exterior surface of bone 310.

Engagement between implant components 326a, 326b and bone 310 according to the principles described above with regard to FIGS. 7A and 7B can be implemented with implants of other shapes as appropriate for a given bone and deformity. For example, the implant component shapes 326a, 326b shown in FIG. 7A could be mere portions of larger implant components having more complex shapes.

Figure 8A:
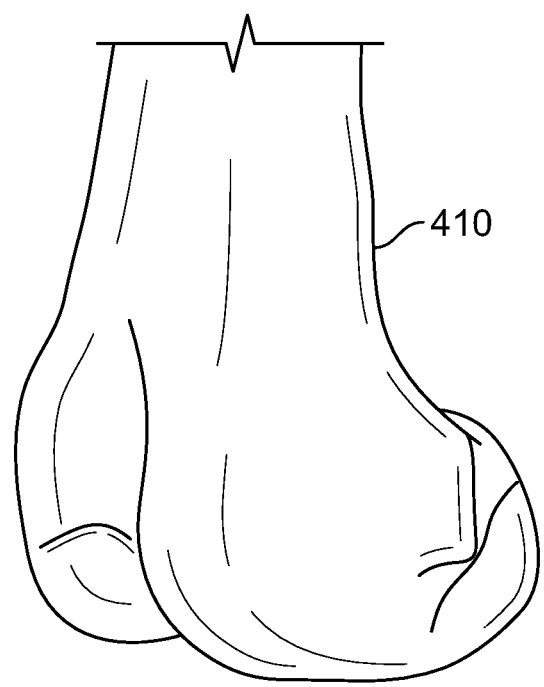
FIGS. 8A-8F illustrate stages in a process of replacing a portion of a bone with interlocking implant components according to an example.
Figure 8B:
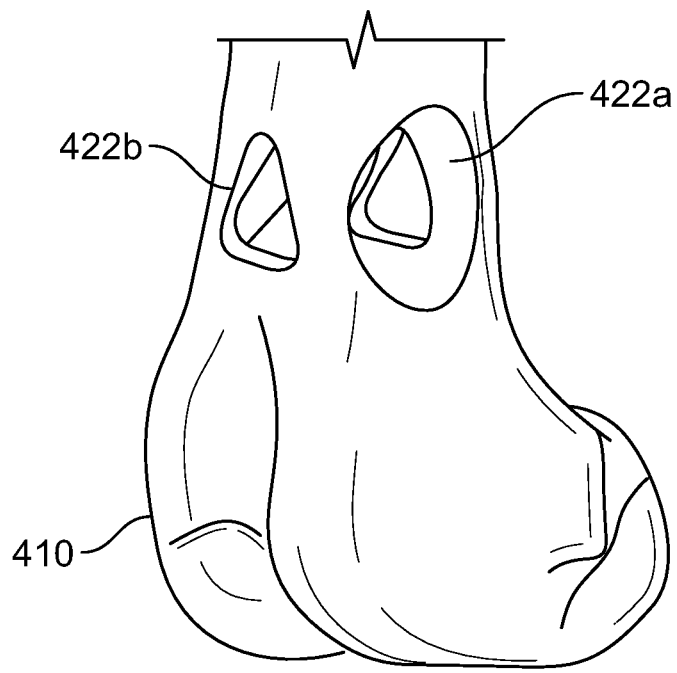

FIGS. 8A-8F illustrate engagement between a first implant component 426a and a second implant component 426b and fitting of first implant component 426a and second implant component 426b to a bone 410, according to another example. The bone 410 of FIG. 8A is a distal end of a femur, by way of example. The bone 410 has a target portion, such as a tumor, proximal of the distal femoral condyles. As shown in FIG. 8A, a first channel 422a and a second channel 422b are cut into bone 410.

The second channel 422b is placed to intersect first channel 422a such that an implant component disposed through second channel 422b can lock in place an implant component disposed through first channel 422a. Both channels 422a, 42b are shaped to accept a respective implant component driven in from an end thereof. However, in all other respects, the shape, size, and location, including respective angles, of first channel 422a and second channel 422b are selected to completely remove the target portion of bone 410 while minimizing the healthy bone removed.

Figure 8C:
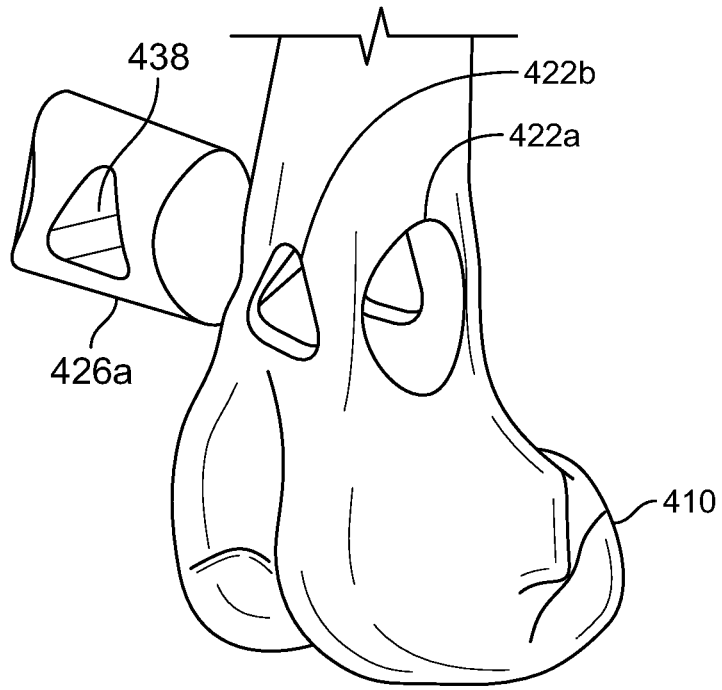
Figure 8D:
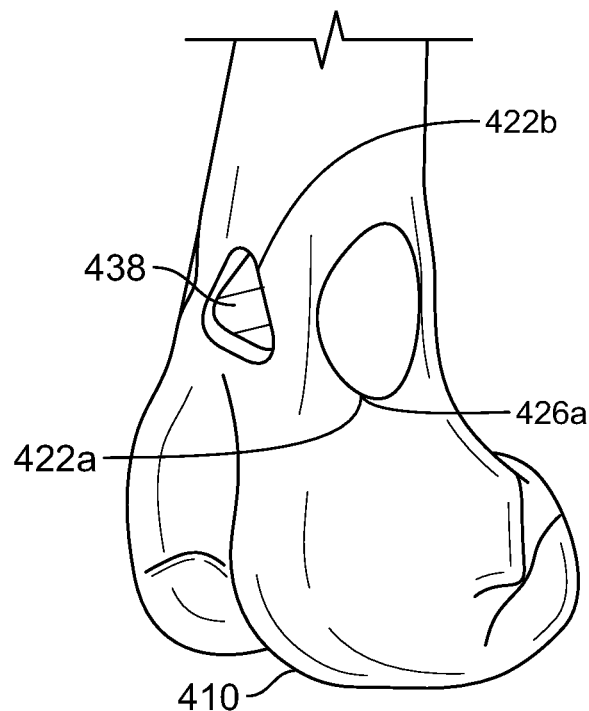
Figure 8E:
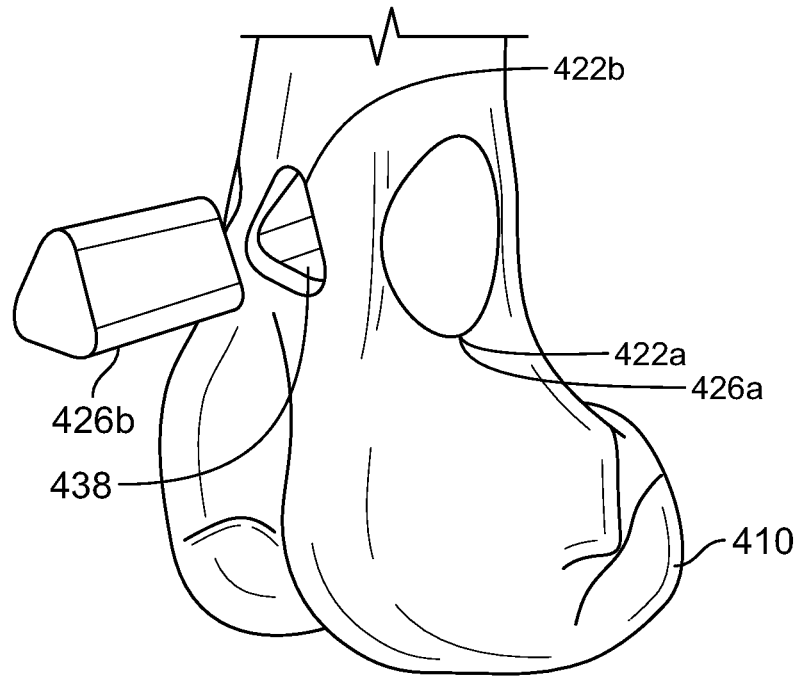
Figure 8F:
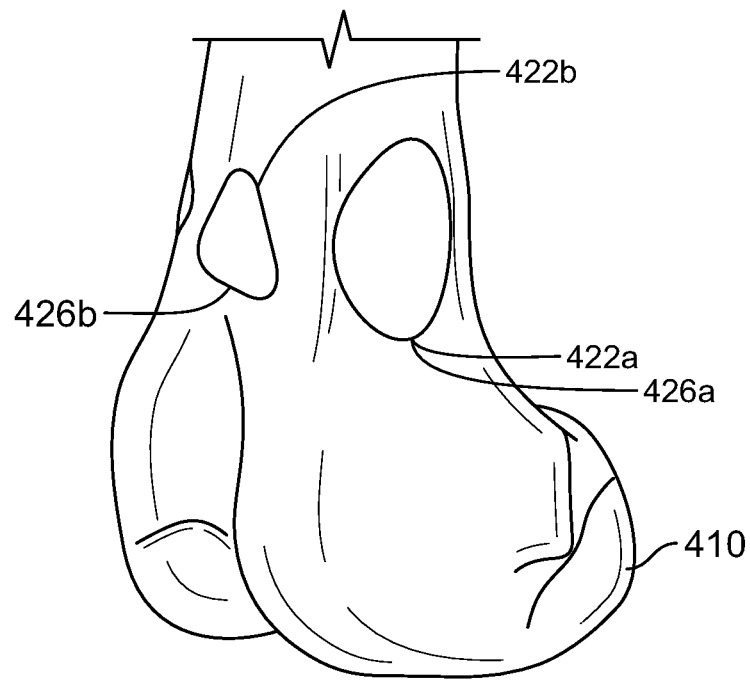

A first implant component 426a and a second implant component 426b, shown in FIGS. 8C-8F, are designed to match planned shapes of first channel 422a and second channel 422b, respectively. The implant components 426a, 426b are shaped both to fill channels 422a, 422b, respectively and to recreate the natural exterior contour of bone 410 when seated within bone 410 as shown in FIG. 8F.

Referring specifically to FIG. 8C first implant component 426a is provided with an aperture 438 corresponding in cross-sectional size and shape to second channel 422b to accept second implant component 426b. In the illustrated example, aperture 438 is shown as an enclosed channel, but in alternative arrangements aperture 438 could be an open notch at an edge of first implant component 426a. As shown in FIG. 8D, first implant component 426a is placed in first channel 422a so that aperture 438 is aligned with second channel 422b. The second implant component 426b can then be aligned with second channel 422b and aperture 438 as shown in FIG. 8E, then driven into place within aperture 438 and second channel 422b as shown in FIG. 8F. When disposed as shown in FIG. 8F, second implant component 426b locks first implant component 426a into place such that the two implant components 426a, 426b fill channels 422a, 422b and recreate the external contour of bone 410 in a healthy state.

In various arrangements, implant components 426a, 426b may be inserted perpendicular or generally perpendicular to one another, as illustrated in FIGS. 8E and 8F, or at any other angle relative to one another. Implant components 426a, 426b may even be inserted parallel to one another if so designed. Insertion angle depends on individual bone geometry, the size, location, and shape of the target region of the bone, and the planning physician's judgment.

Figure 9A:
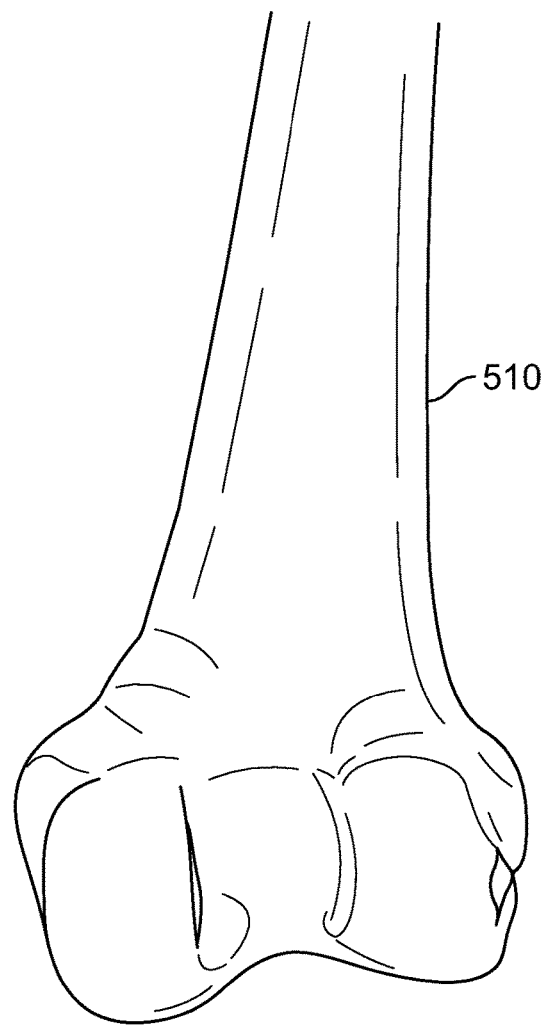
FIGS. 9A-9G illustrate stages in a process of replacing a portion of a bone with interlocking implant components according to another example.
Figure 9B:
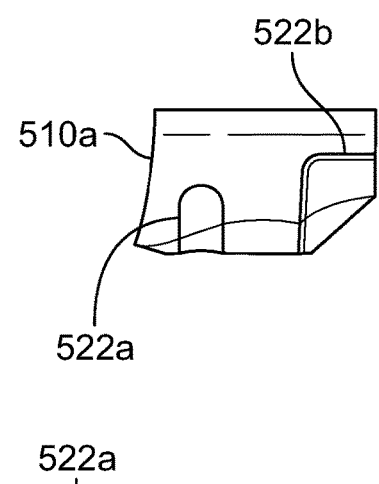
Figure 9B:
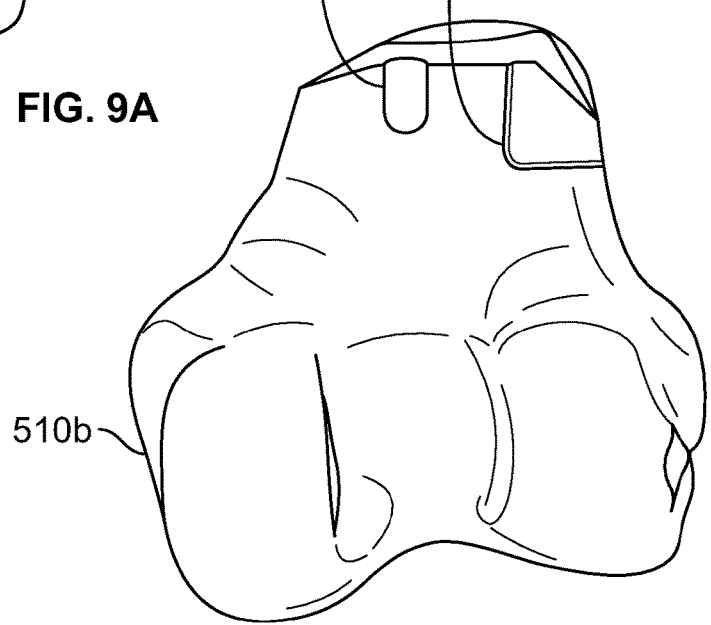
Figure 9C:
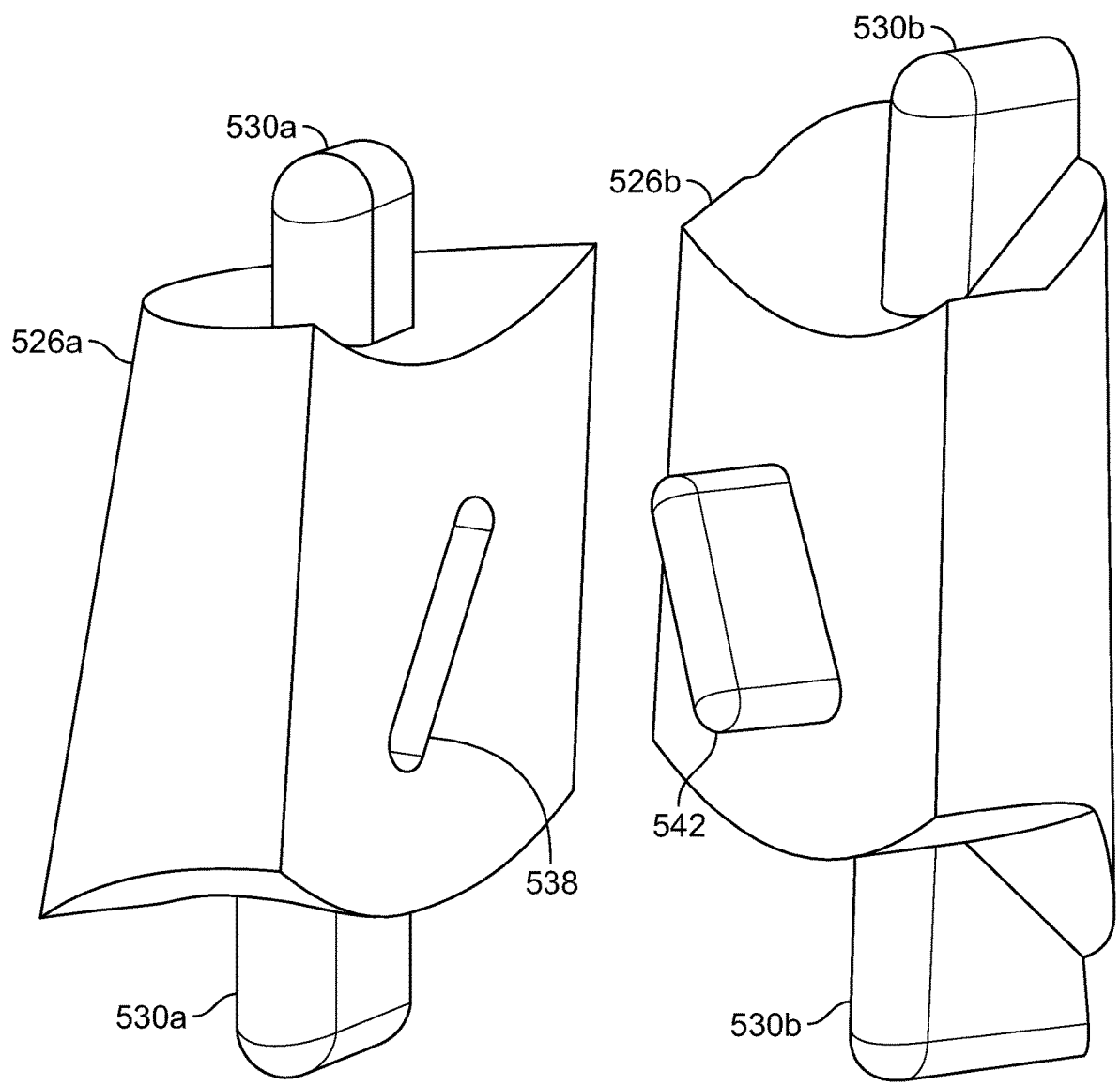

Implants can also be used to rejoin portions of a bone 510 separated during removal of a target portion. For example, bone 510 of FIG. 9A includes a target portion that can be most effectively removed by separating the bone into a proximal portion 510a and a distal portion 510b, as shown in FIG. 9B. The bone 510 in the illustrated example is a distal portion of a femur, but the ideas presented here can be applied to other bones as well. A blind hole 522a and a slot 522b are cut into each of the proximal portion 510a and distal portion 510b. The number, shape, and placement of holes and slots in each portion 510a, 510b, beyond what is shown in FIG. 9B, may be chosen on a case-by-case basis to remove target portions of bone 510 while preserving as much healthy bone as possible.

A first implant component 526a and a second implant component 526b are constructed to combine together to replace the resected portion of bone 510. The implant components 526a, 526b are thus constructed to be joinable so as to form a shape with proximal and distal contours matching the cut faces of proximal portion 510a and distal portion 510b of bone, respectively, and an outer perimeter recreating the shape of a healthy bone.

The first implant component 526a includes pegs 530a receivable in blind holes 522a, and second implant component 526b includes flanges 530b receivable in slots 522b. The first implant component 236a also defines a recess 538 into which a tab 542 of second implant component 526b is receivable. The respective features of first implant component 526a and second implant component 526b of the illustrated example are chosen in a patient-specific manner to match the cuts made to bone portions 510a, 510b as shown in FIG. 9B.

Figure 9D:
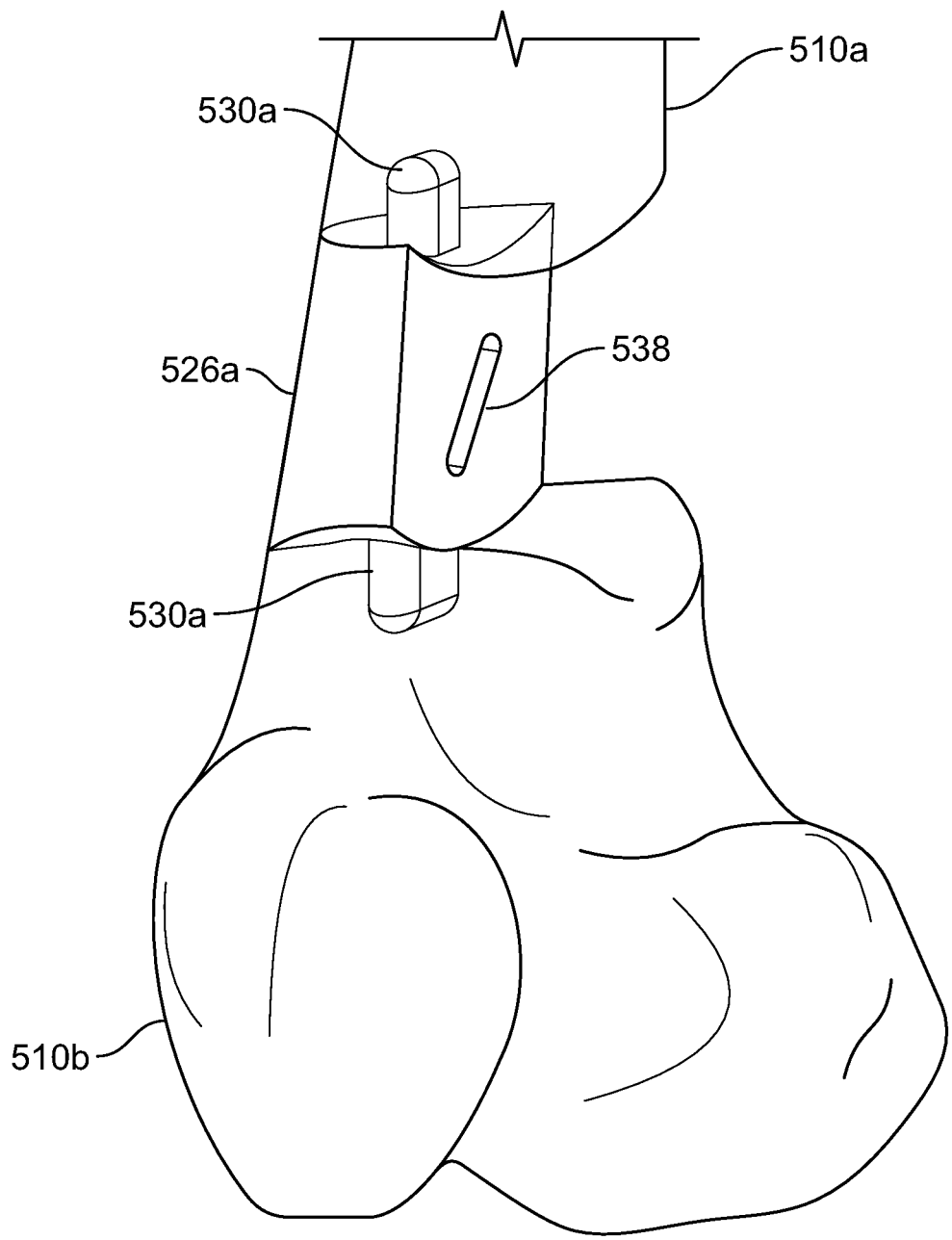

The first implant component 526a can be placed as shown in FIG. 9D, with a peg 530a received in blind hole 522a of each bone portion 510a, 510b, by briefly distracting bone portions 510a, 510b as first implant component 526a is moved into place, then reducing bone portion 510a, 510b toward one another.

Figure 9E:
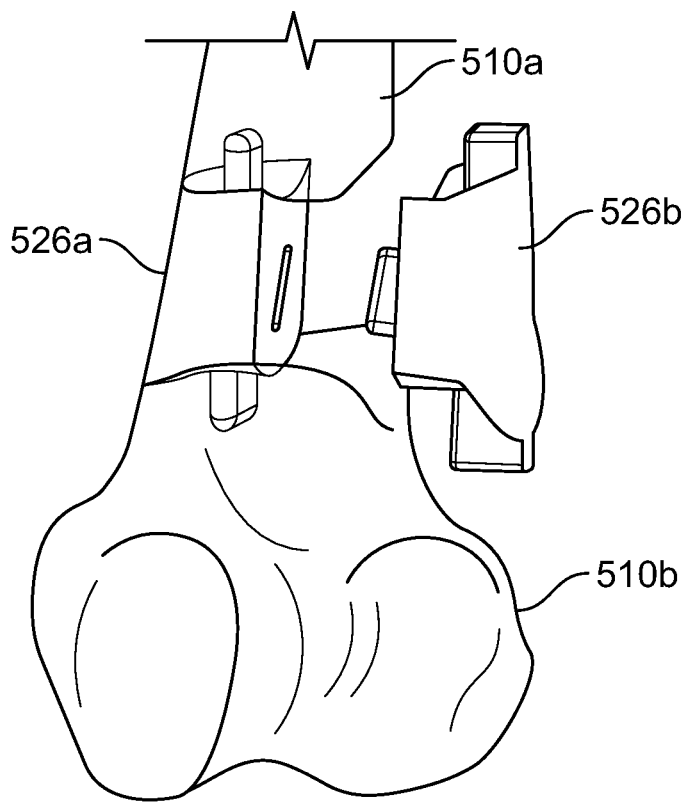
Figure 9F:
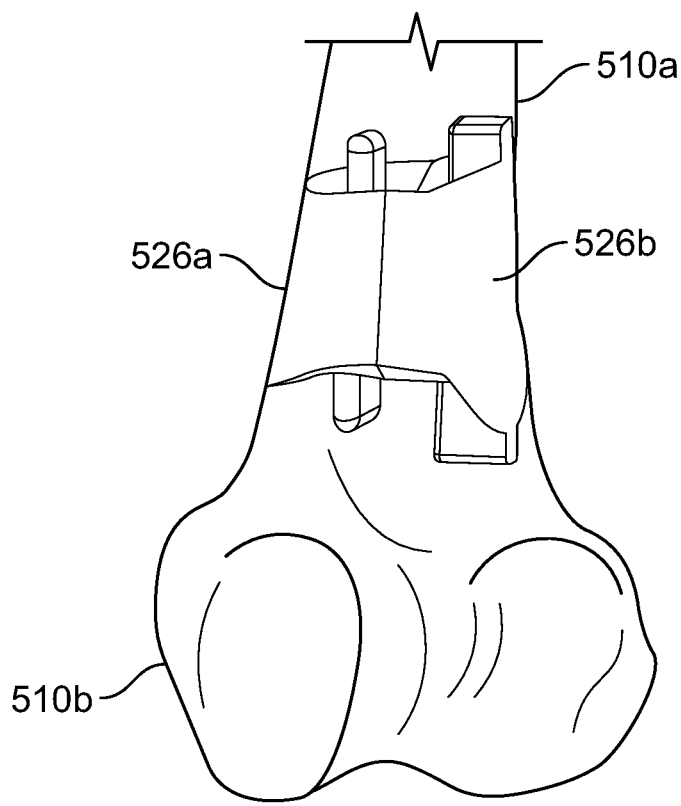
Figure 9G:
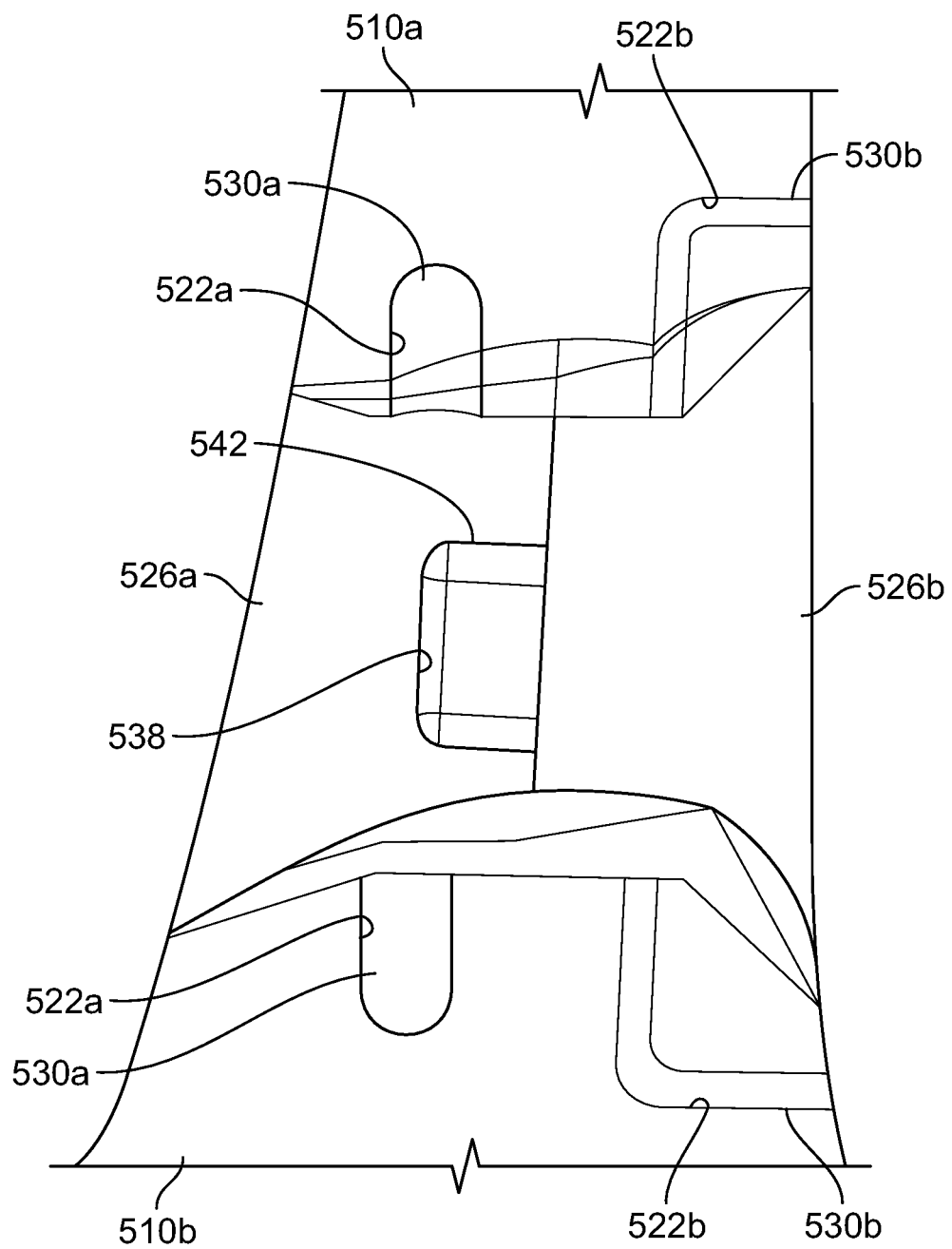

After first implant component 522a is in place, second implant component 522b can be slid from beside bone portions 510a, 510b, as shown in FIG. 9E, into engagement with first implant component 522a and bone portions 510a, 510b, as shown in FIG. 9F. When second implant component 522b is engaged with first implant component 522a and bone portions 510a, 510b, flanges 530b are disposed within slots 522b for bone portions 510a, 510b, and tab 526a is disposed within recess 538, as shown in FIG. 9G.

Figure 10A:
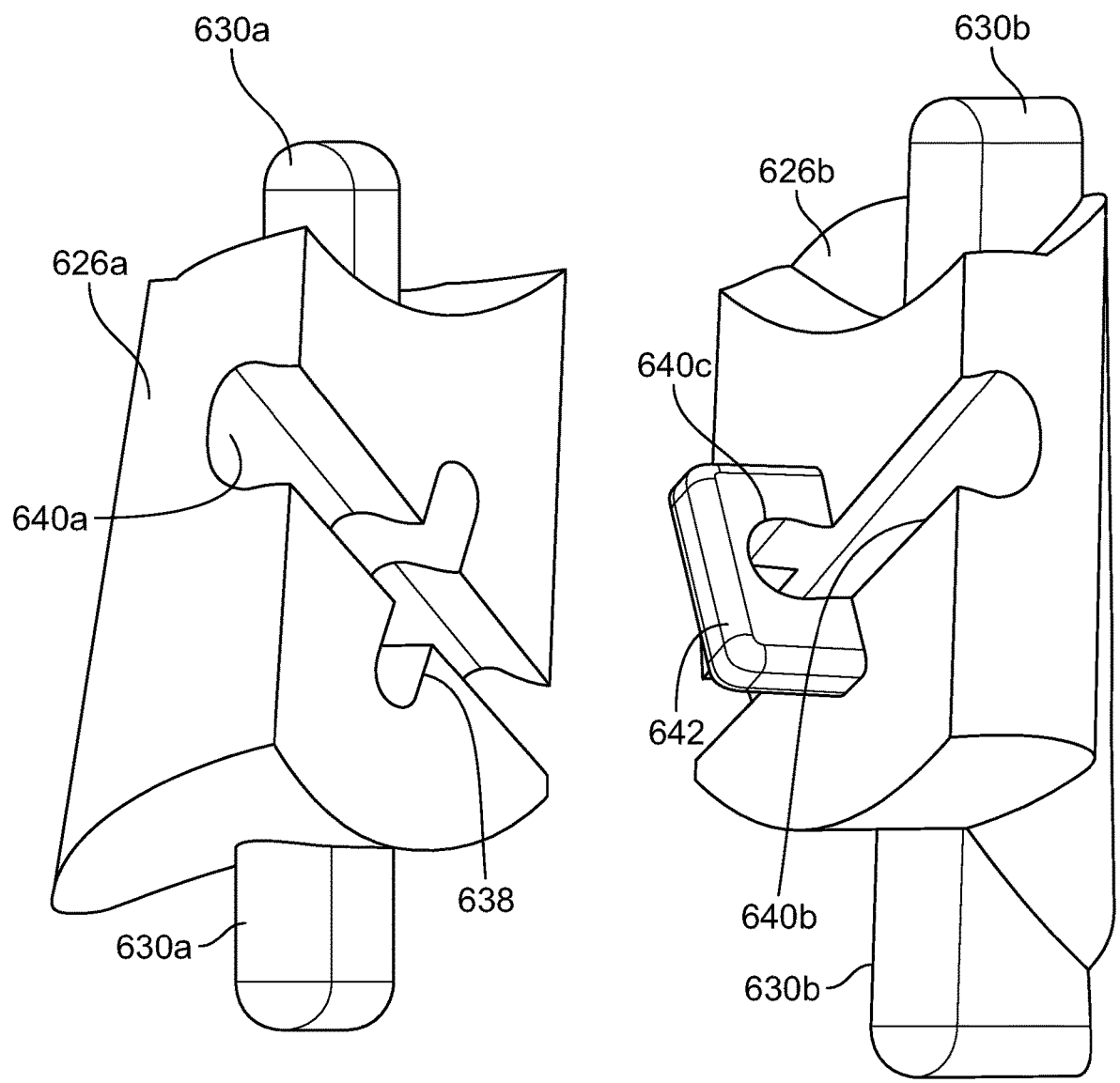
FIG. 10A illustrates two interlocking implant components.
Figure 10B:
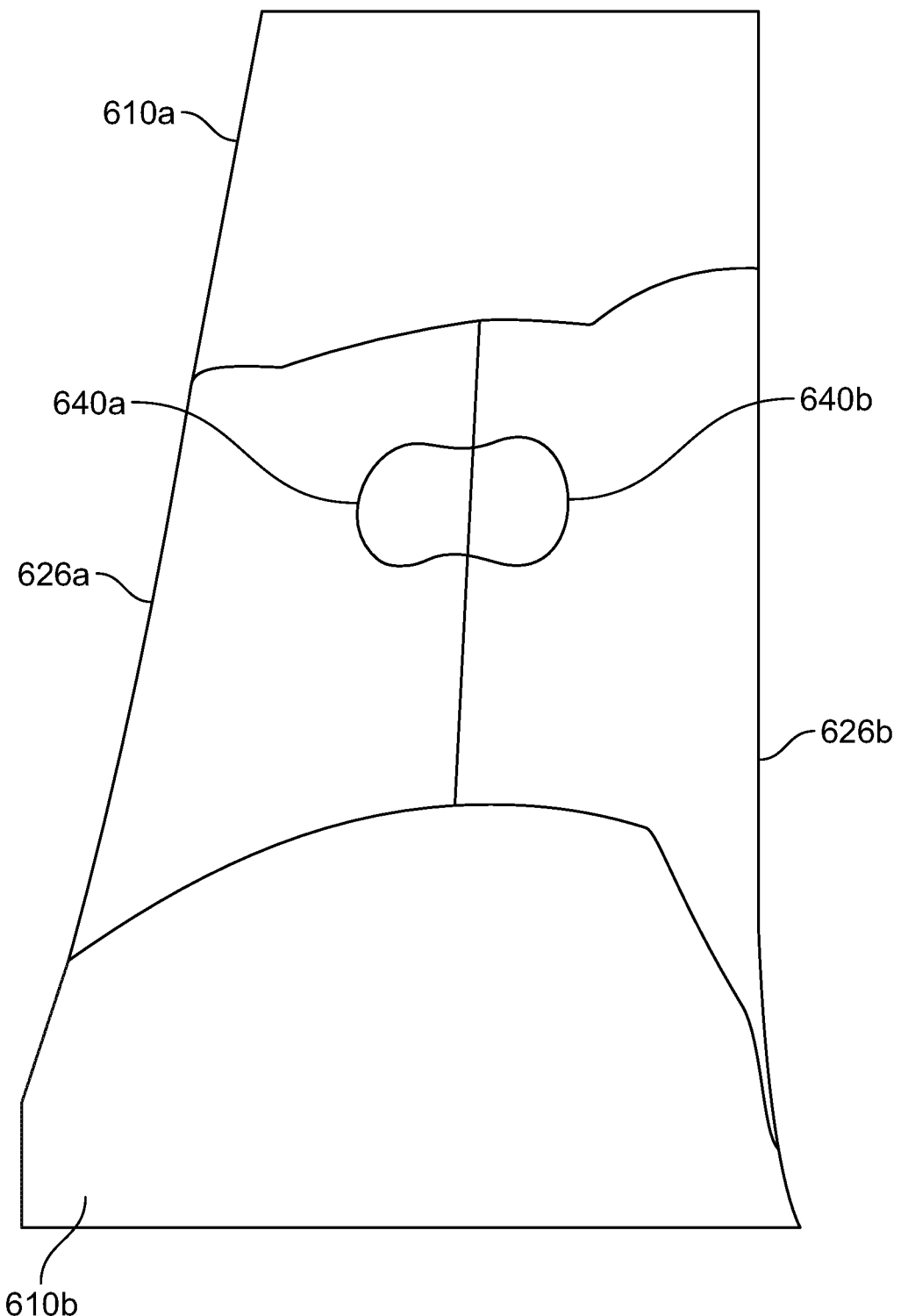
FIG. 10B illustrates the interlocking implant components of FIG. 10A seated between portions of a bone.
Figure 10C:
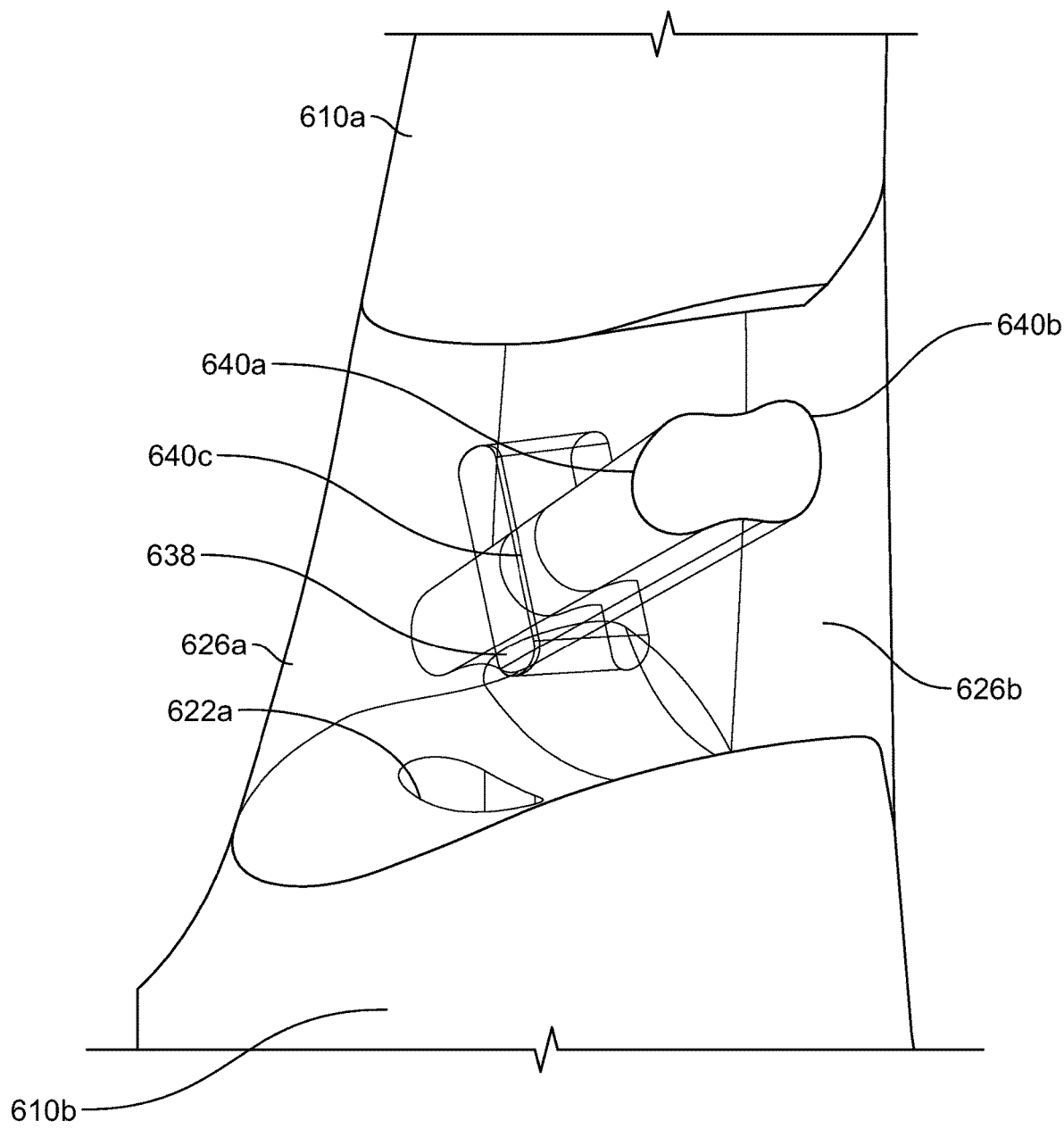
FIG. 10C illustrates the interlocking implant components of FIG. 10A seated between portions of a bone and secured by another implant component.

FIGS. 10A-10C illustrate an alternative arrangement of the example of FIGS. 9A-9F. Between the arrangements of FIGS. 9A-9F and 10A—10C, like numerals refer to like elements (i.e., pegs 530a and 530b are generally alike) except where stated or shown otherwise. As such, not all numerals of FIGS. 10A-10C will be referenced herein.

Referring to FIG. 10A specifically, a first opening or channel 640a extends across a mating face of first implant component 626a, and a second opening or channel 640b extends across a corresponding mating face of second implant component 626b. Channels 640a and 640b are formed as elongate channels or notches such that they are not fully enclosed about their longitudinal axis. Neither channel 640a, 640b, which may be in the form of an elongate groove or notch, is widest at the respective mating face. The tab 642 includes a hole 640c open to second channel 640b and matching first channel 640a in shape and size.

As shown in FIG. 10B, channels 640a, 640b are aligned with one another so as to form a hole extending through a body formed when the two implant components 626a, 626b are engaged with tab 642 disposed in recess 638. Because hole 640c matches the shape and size of first channel 640a, the hole defined by channels 640a, 640b is not interrupted by tab 642. Because neither channel 640a, 640b is widest at the mating face of the respective implant component 626a, 626b, the hole defined because neither channel 640a, 640b is widest at the mating face of the respective implant component 626a, 626b, the hole defined by channels 640a, 640b has an axial cross-sectional shape resembling a bow-tie or the numeral "8" relative to a longest axis along which the hole extends.

As shown in FIG. 10C, a pin 646 with an axial cross-section matching that of the hole defined by channels 640a, 640b may be provided to lock implant components 626a, 626b together. Because the hole defined by channels 640a, 640b has a bow-tie or numeral "8" shaped cross section, implant components 626a, 626b cannot separate while pin 646 is disposed in the hole. Because pin 646 also extends through hole 640c in tab 642 when pin 646 is disposed in the hole as shown in FIG. 10C, pin 646 also prevents disengagement of implant components 626a, 626b in alternative arrangements where the axial cross-sectional shape of the second channel 640b does not, itself, retain pin 646.

When disposed to connect implant components 626a, 626b as shown in FIG. 10C, pin 646 also forms part of the external contour of a prosthesis that replaces the removed bone. Ends of pin 646 may therefore be contoured according to patient-specific data, such as, for example, imaging data, much like implant components 626a, 626b.

Though the hole defined by channels 640a, 640b extends entirely through the body defined by implant components 626a, 626b in the illustrated example, in alternative arrangements the hole might be closed on one end to prevent pin 646 from sliding out. In other alternatives, the hole might be tapered such that pin 646 wedges into place.

Figure 11A:
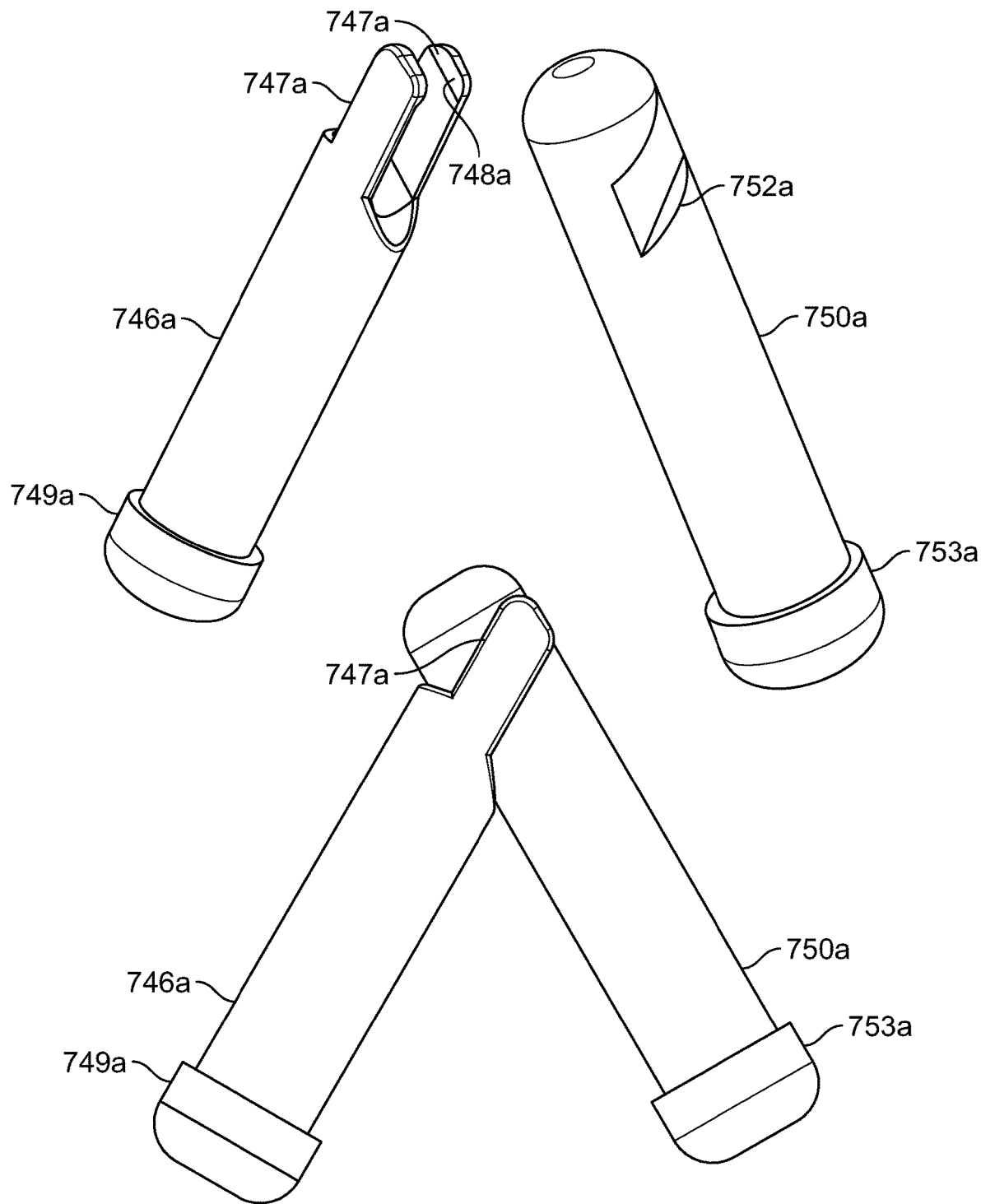
FIG. 11A illustrates a pair of interlocking pins in both an unengaged and an engaged state.

Turning to FIG. 11A, mutually interlocking pins may be provided to secure an implant to bone. A first gripping pin 746a includes two resiliently flexible first arms 747a extending from an end of first gripping pin 746a and spaced apart from one another. Each first arm 747a includes an inner rib 748a (only one being visible from the perspective of FIG. 11A) on a surface facing the other first arm 747a. The first ribs 748a may be angled, as illustrated, according to an intended angle of engagement with a first receiving pin 750a, described below. The first gripping pin 746a includes a first gripping pin head 749a at an end opposite from first arms 747a, first gripping pin head 749a being the portion of first gripping pin 746a having the greatest diameter.

A first receiving pin 750a is also provided. The first receiving pin 750a includes a first receiving pin head 753a defining a portion of first receiving pin 750a having a greatest diameter. The first receiving pin 750a includes channels 752a, which may be in the form of an elongate groove or notch, on opposite sides thereof (only one being visible from the perspective of FIG. 11A), the channels having a width equal to or slightly greater than a width of first arms 747a. A neck portion of first receiving pin 750a is defined between the two channels 752a. The neck portion has a thickness that is equal to, or about equal to, a space between first arms 747a. The first gripping pin 746a may therefore be caused to grip first receiving pin 750a by causing first arms 747a to be received within channels 752a, with ribs 748a preventing release. For example, first gripping pin 746a may be forced relative to first receiving pin 750a to cause first arms 747a to deflect to allow first receiving pin 750a to pass between ribs 748a. When first gripping pin 746a reaches the position relative to first receiving pin 750a shown in the lower portion of FIG. 11A, first arms 747a snap back toward their rest position and first ribs 748a lie against a respective portion of an outer contour of first receiving pin 750a, inhibiting release of first receiving pin 750a from between first arms 747b.

A second gripping pin 746b and second receiving pin 750b operate similarly, and may be used in addition to or in the alternative of first gripping pin 746a and second receiving pin 750a.

Figure 11B:
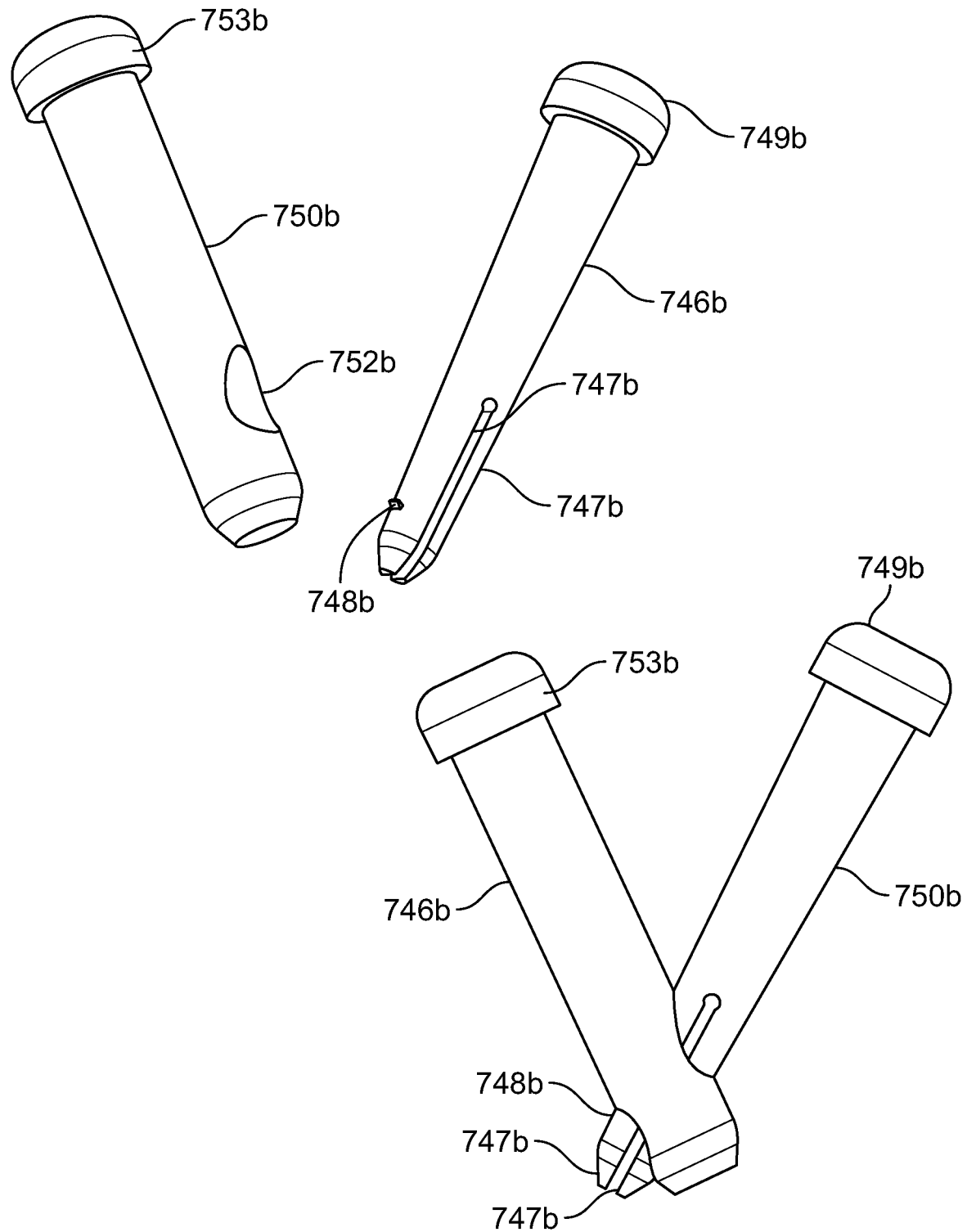
FIG. 11B illustrates another pair of interlocking pins in both an unengaged and an engaged state.

The second gripping pin 746b includes two spaced apart, resiliently flexible second arms 747b extending from one end, and a second gripping pin head 749b at another end, second gripping pin head 749b defining a portion of second gripping pin 746b of greatest diameter. Each second arm 747b includes a respective second rib 748b (only one being visible from the perspective of FIG. 11B) on a surface facing away from the other second arm 747b. The second ribs 748b may be at different locations along their respective second arm 747b from one another according to an intended angle of engagement between second gripping pin 746b and second receiving pin 750b. In the illustrated example, second gripping pin 746b and second arms 747b taper to a point at an end opposite from second gripping pin head 749b to fit in a hole 752b of second receiving pin 750b, but in other arrangements second gripping pin 746b may have a constant or substantially constant diameter along most or all of its length.

The second receiving pin 750b includes a second receiving pin head 753b defining a portion of second receiving pin 750b having a greatest diameter. The second receiving pin 750b also includes a hole 752b through which second arms 747b may be received. The second gripping pin 746b may be engaged with second receiving pin 750b by pressing second arms 747b into hole 752b such that second arms 747b deflect toward one another to allow second ribs 748b to pass into hole 752b. When second gripping pin 746b is fully inserted, second arms 747b travel back toward their respective resting positions and second ribs 748b engage an outer surface of second receiving pin 750b just outside a perimeter of hole 752b, inhibiting withdrawal of second gripping pin 746b from hole 752b.

Figure 11C:
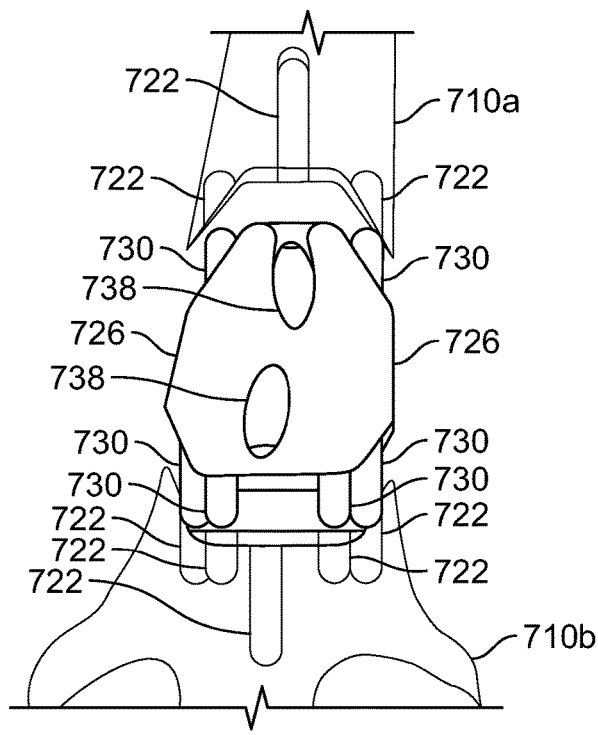
FIG. 11C is a back elevation view if an implant component positioned between separated portions of a bone.
Figure 11D:
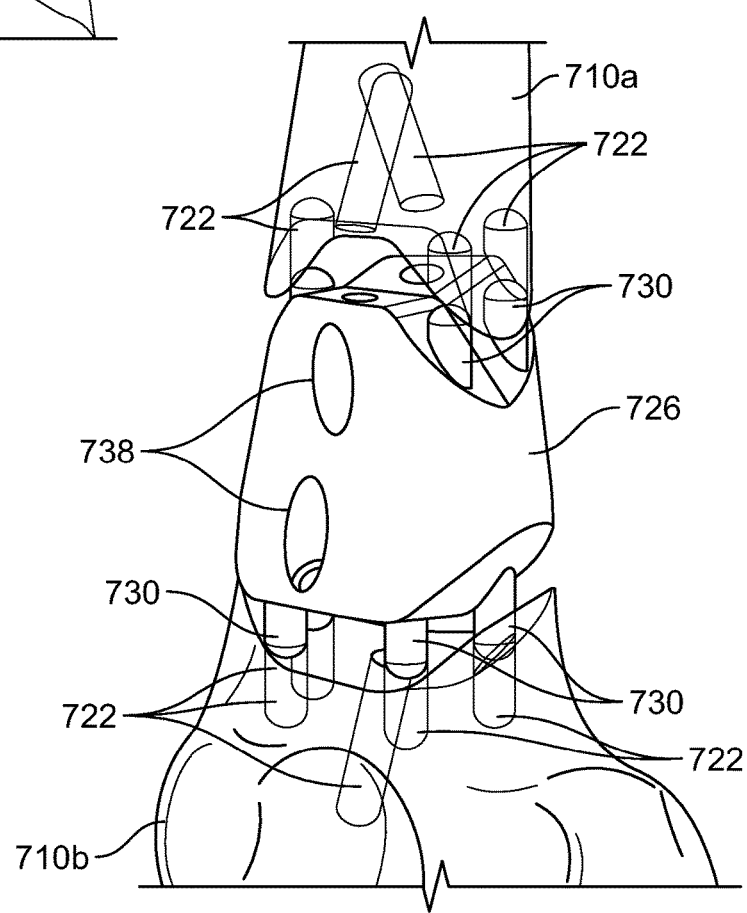
FIG. 11D is an oblique elevation view of the implant component of FIG. 11C positioned between the separated portions of the bone.

Gripping pins 746a, 750b and receiving pins 750a, 750b may be used to lock in place a patient-specific implant or implant component according to any example of the present disclosure if that implant or implant component includes or is modified with suitable, multiple stage holes. An exemplary implant or implant component 726, which may be patient-specific as described with regard to any of the examples above, is illustrated in FIGS. 11C and 11D. The implant 726 includes pegs 730 receivable in holes 722 drilled into bone portions 710a, 710b that implant 726 will connect. The implant 726 may be placed such that pegs 730 are received in holes 722 by temporarily distracting bone portions 710a, 710b while implant 726 is moved between bone portions 710a, 710b, then reducing bone portions 710a, 710b into engagement with implant 726.

The implant 726 also includes apertures 738 for receiving gripping pins 746a 746b and receiving pins 750a, 750b. The apertures 738 are aligned with holes 722 in bone portions 710a, 710b that do not correspond to any pegs 730. The holes 722 aligned with apertures 738 intersect one another at the same angle as a corresponding pair of a first gripping pin 746a and a first receiving pin 750a or a second gripping pin 746b and second receiving pin 750b. As shown in FIGS. 11E-11H, implant 726 can be secured to bone portions 710a, 710b by placing gripping pins 746a, 746b and receiving pins 750a, 750b such that they interlock within the bone while disposed through apertures 738 and intersecting holes 722. The apertures 738 are each multiple-stage holes, having an outer stage larger in diameter than pin heads 749a, 749b, 753a, 753b, and an inner stage nearer holes 722 smaller in diameter than pin heads 749a, 749b, 753a, 753b. The pins 746a, 746b, 750a, 750b can therefore seat within apertures 738 with the respective pin head 749a, 749b, 753a, 753b disposed in the larger stage of the respective aperture.

Figure 11E:
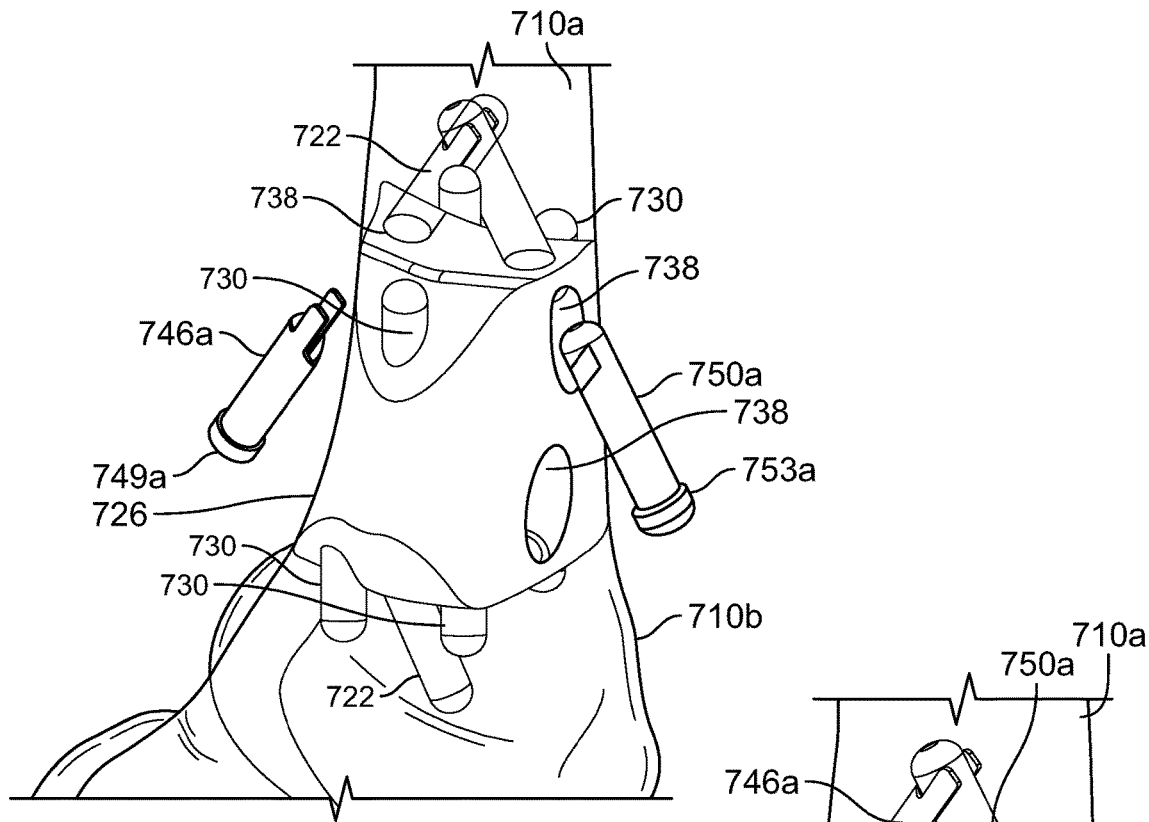
FIGS. 11E and 11F illustrate stages in a process of fastening the implant component of FIG. 11C to bone with the pins of FIG. 11A.
Figure 11F:
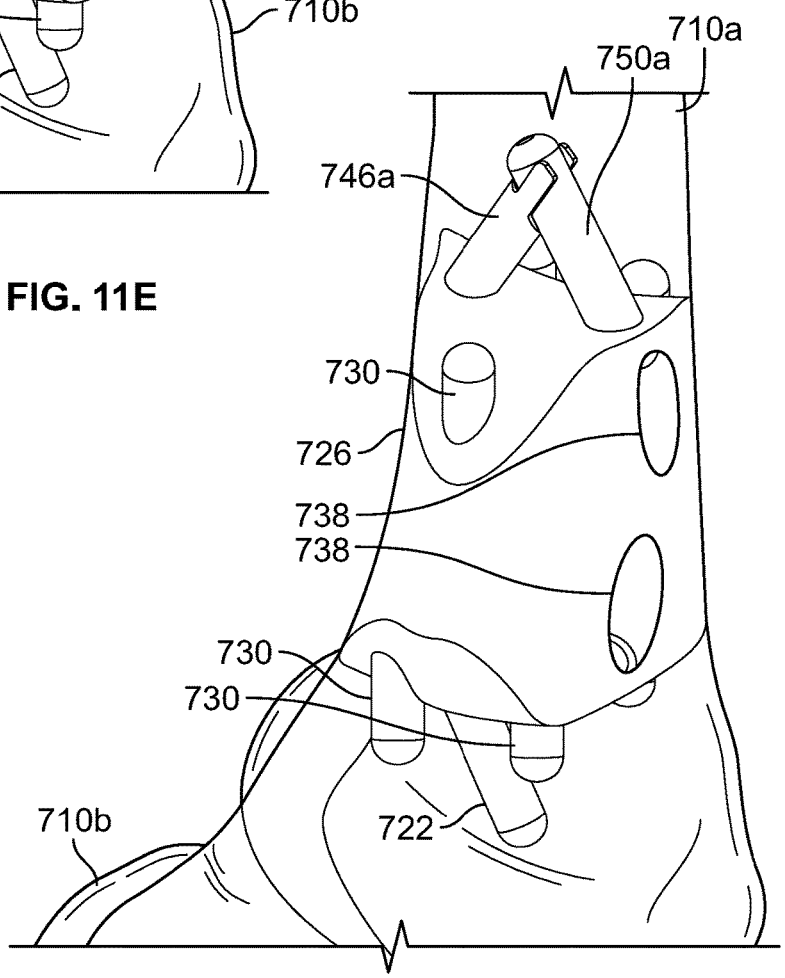
Figure 11G:
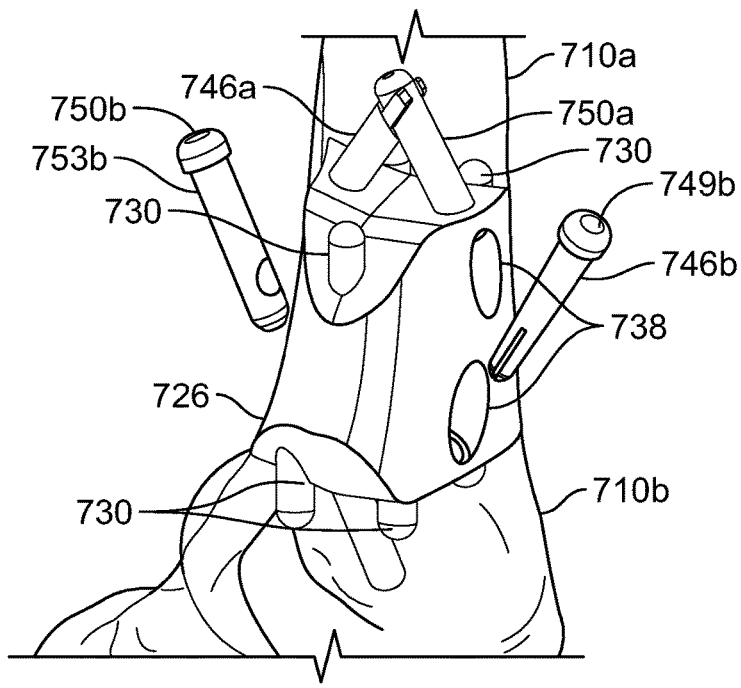
FIGS. 11G and 11H illustrate stages in a process of fastening the implant component of FIG. 11C to bone with the pins of FIG. 11B.
Figure 11H:
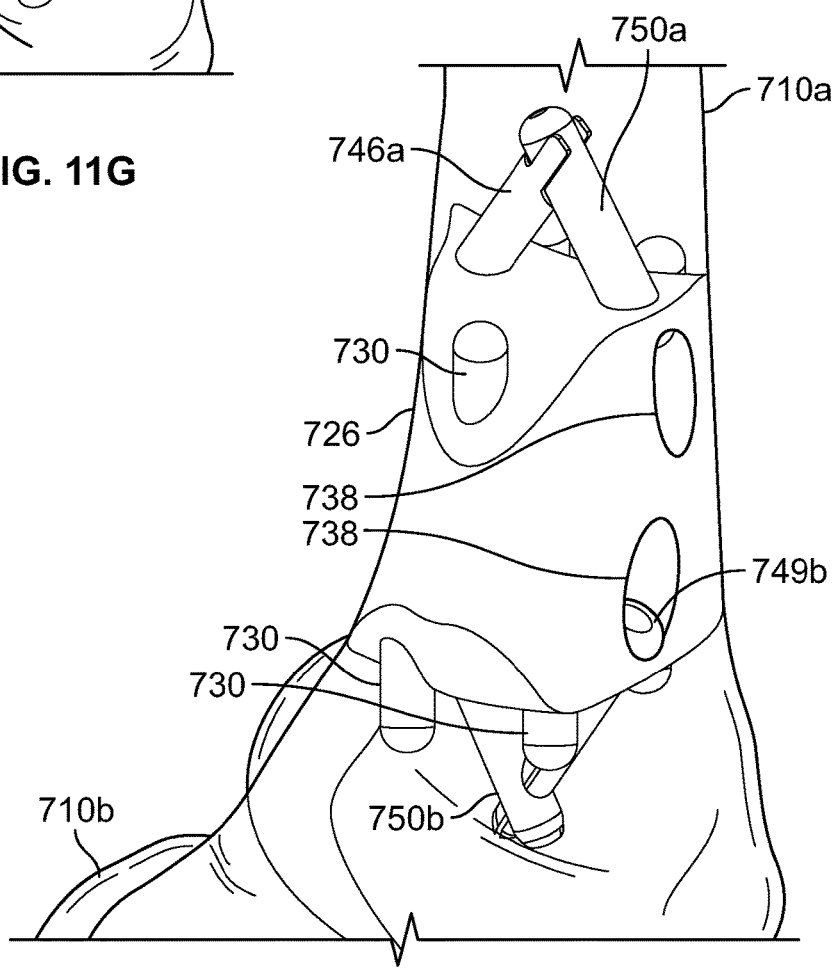

In the illustrated example, first gripping pin 746a and first receiving pin 750a are disposed through two of apertures 738 and engaged within first bone portion 710a as shown in FIGS. 11E and 11F before second gripping pin 746b and second receiving pin 750b are disposed through another two of apertures 738 and engaged within second bone portion 710b as shown in FIGS. 11G and 11H. However, in other examples, the pins may be inserted in any order. Moreover, in other arrangements, different types of interlocking pins may be used in any quantity and any combination according to the quantity of bone removed and the physician's preference. For example, an implant may be locked to bone with multiple pairs of first gripping pins 746a and first receiving pins 750a, multiple pairs of second gripping pins 746b and multiple pairs of receiving pins 750b, pairs of interlocking pins according to other designs, or any combination thereof. Further still, mutually interlocking pins according to the foregoing examples, or pins operating on similar principles, may be used with implants of differing shape than implant 726.

Figure 12A:
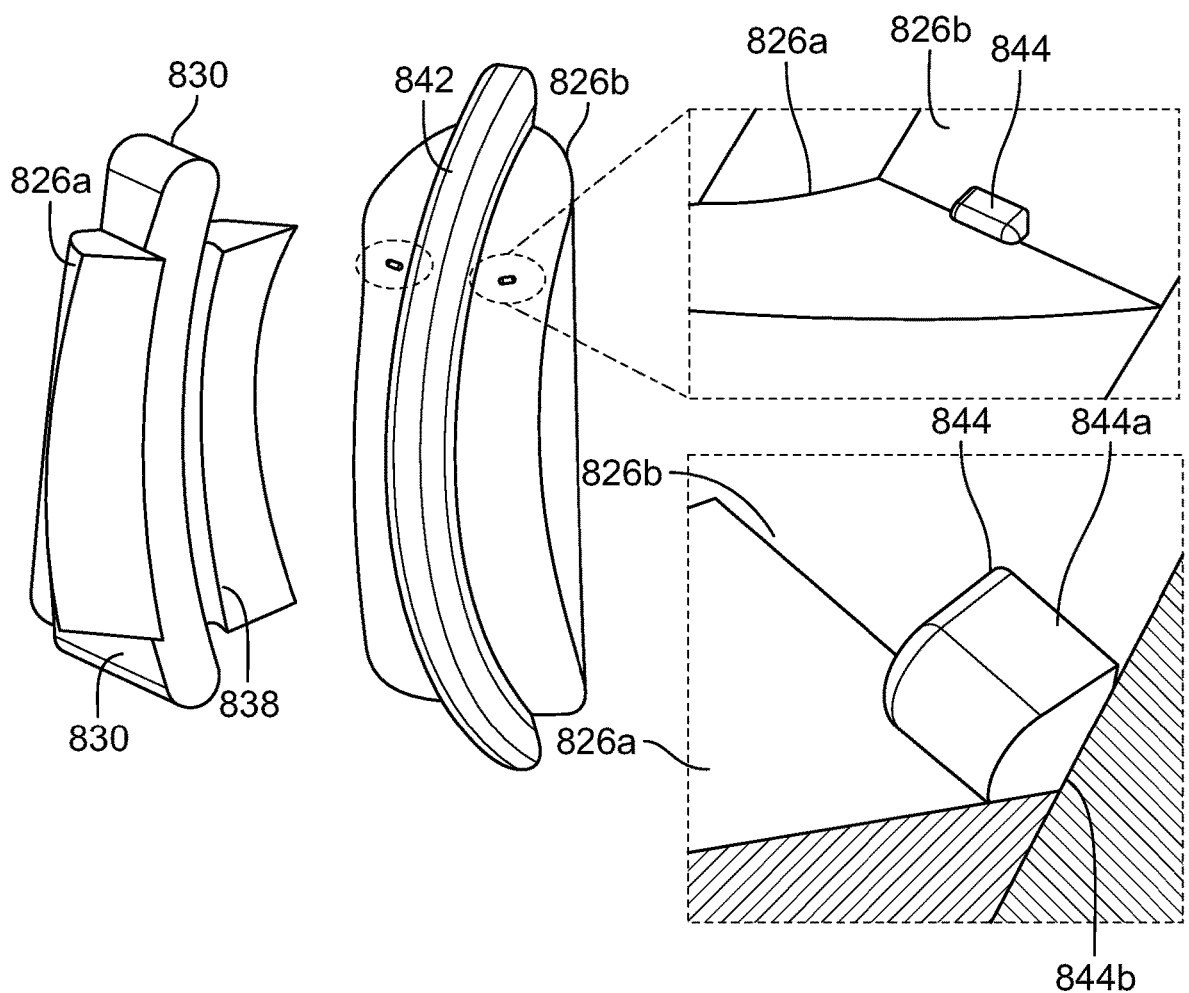
FIG. 12A illustrates a pair of interlocking implant components according to another example.

In another example shown in FIG. 12A, a first implant component 826a includes a channel 838 for receiving a rib 842 of a second implant component 826b. The first implant component 826a also includes flanges 830a for engaging slots cut into bone.

Figure 12B:
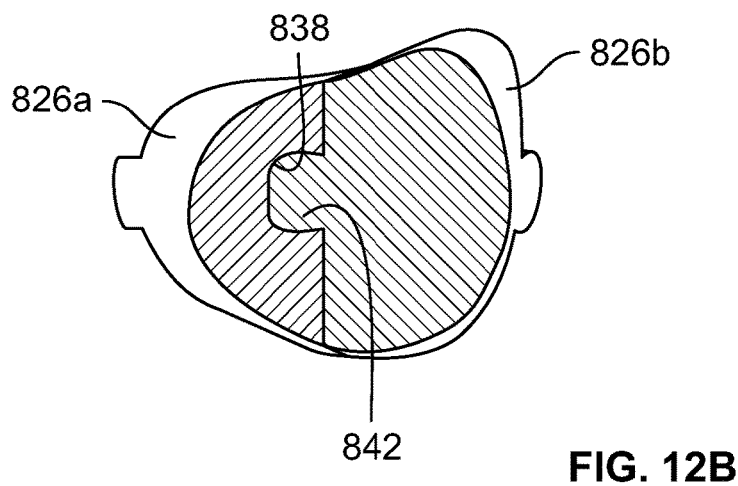
FIG. 12B is a cross-sectional view of the implant components of FIG. 12A in a mutually engaged configuration.

Turning to FIG. 12B, the widest portion of channel 830 is not at the mating face of first implant component 826a. Similarly, the widest portion of rib 842 is not at the mating face of second implant component 826b. This causes rib 842 to have a dovetailing fit within channel 838, preventing implant components 826a, 826b from translating out of engagement when interlocked as shown in FIG. 12B.

Returning to FIG. 12A, second implant component 826b includes tabs 844 on either side of rib 842 to limit rotation of implant components 826a, 826b relative to one another while rib 842 is received in channel 838. Assembly of implant components 826a, 826b therefore may be accomplished by insertion of an end of rib 842 furthest from tabs 844 into an end of channel 838, followed by rotation of second implant component 826b relative to first implant component 826a to drive rib 842 further into channel 838 until tabs 844 abut a surface of first implant component 826a.

In arrangements wherein tabs 844 are elastically flexible, assembly of implant components 826a, 826b may begin by insertion of an end of rib 842 closest to tabs 844 into an end of channel 838 followed by rotation of second implant component 826b relative to first implant component 826a. Because tabs 844 in such arrangements are flexible, they may deform against first implant component 826a to allow an upper end of rib 842, from the perspective of FIG. 12A, to travel from a lower end of channel 838 to an upper end of channel 838.

Tabs 844 may only be able to deform against first implant component 826a in one direction. In the illustrated example, tabs 844 each have a sloped upper surface from the perspective of FIG. 12A that creates an obtuse angle 844a with the body of second implant component 826b and a lower surface that creates an acute angle 844b with the body of second implant component 826b. Tabs 844 of the illustrated arrangement may therefore only deform against first implant component 826a to pass by first implant component 826a while the upper end of rib 842 travels from the lower end to the upper end of channel 838. However, when ribs 844 abut an upper surface of first implant component 826a as shown in the enlarged portions of FIG. 12A, ribs 844 may be unable to deform far enough to permit the upper end of rib 842 to travel any further downward relative to first implant component 826a. Ribs 844 of the illustrated arrangement therefore act to prevent rotation of second implant component 826b relative to first implant component 826a while rib 842 is within channel 838 in one direction only. Though not illustrated, second implant component 826b may also include one or more additional, opposed ribs at a lower end that extend in a generally opposite direction to that of the illustrated ribs 844, and thus prevent rotation in a direction opposite to that which is prevented by the illustrated ribs 844. The opposed sets of ribs may thus cooperate to prevent rotation and disengagement of the implant components 826a, 826b relative to one another after rib 842 reaches a position within channel 838 wherein first implant component 826a is trapped between the opposed sets of ribs.

Figure 12C:
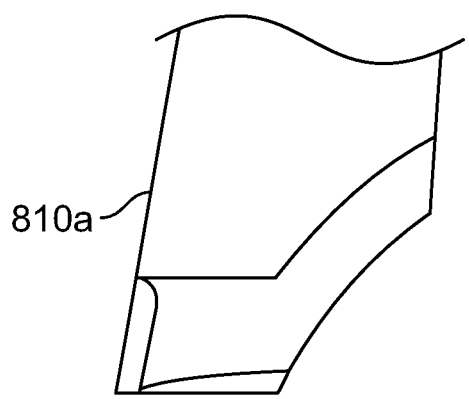
FIG. 12C is a translucent back elevation view of two portions of a bone prepared to engage the implant components of FIG. 12A.
Figure 12C:
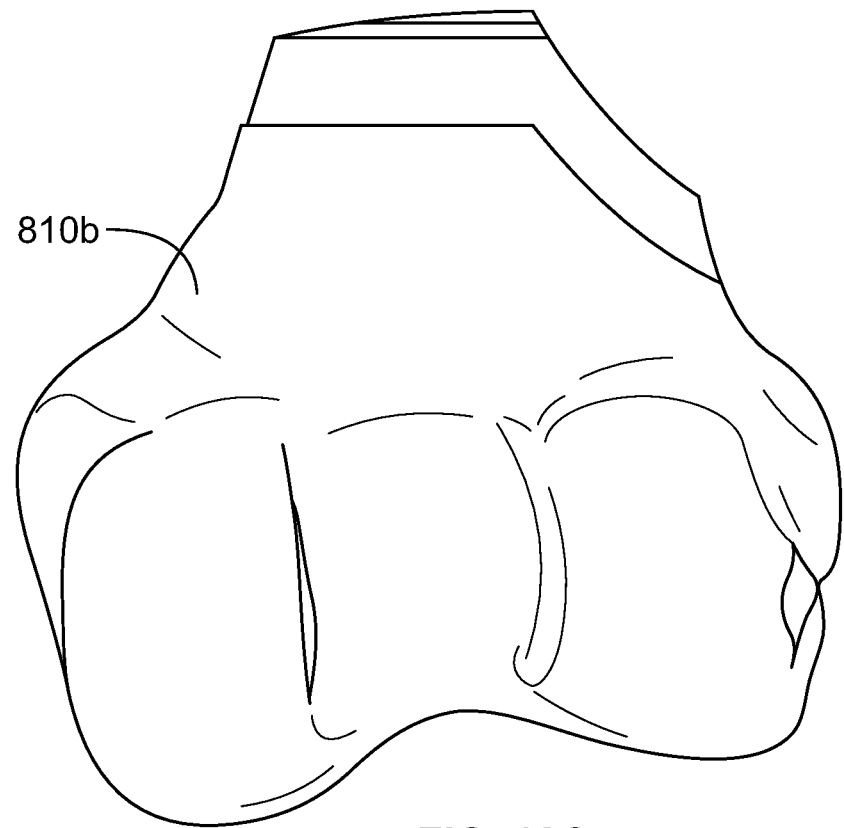

FIG. 12C shows an example of a first bone portion 810a and a second bone portion 810b prepared with respective slots to receive flanges 830a and rib 842 with a dovetailing fit. The cuts to the bone are made according to the size and shape of target bone that must be removed, and implant components 826a, 826b are designed in view of the plans for the cuts.

Figure 12D:
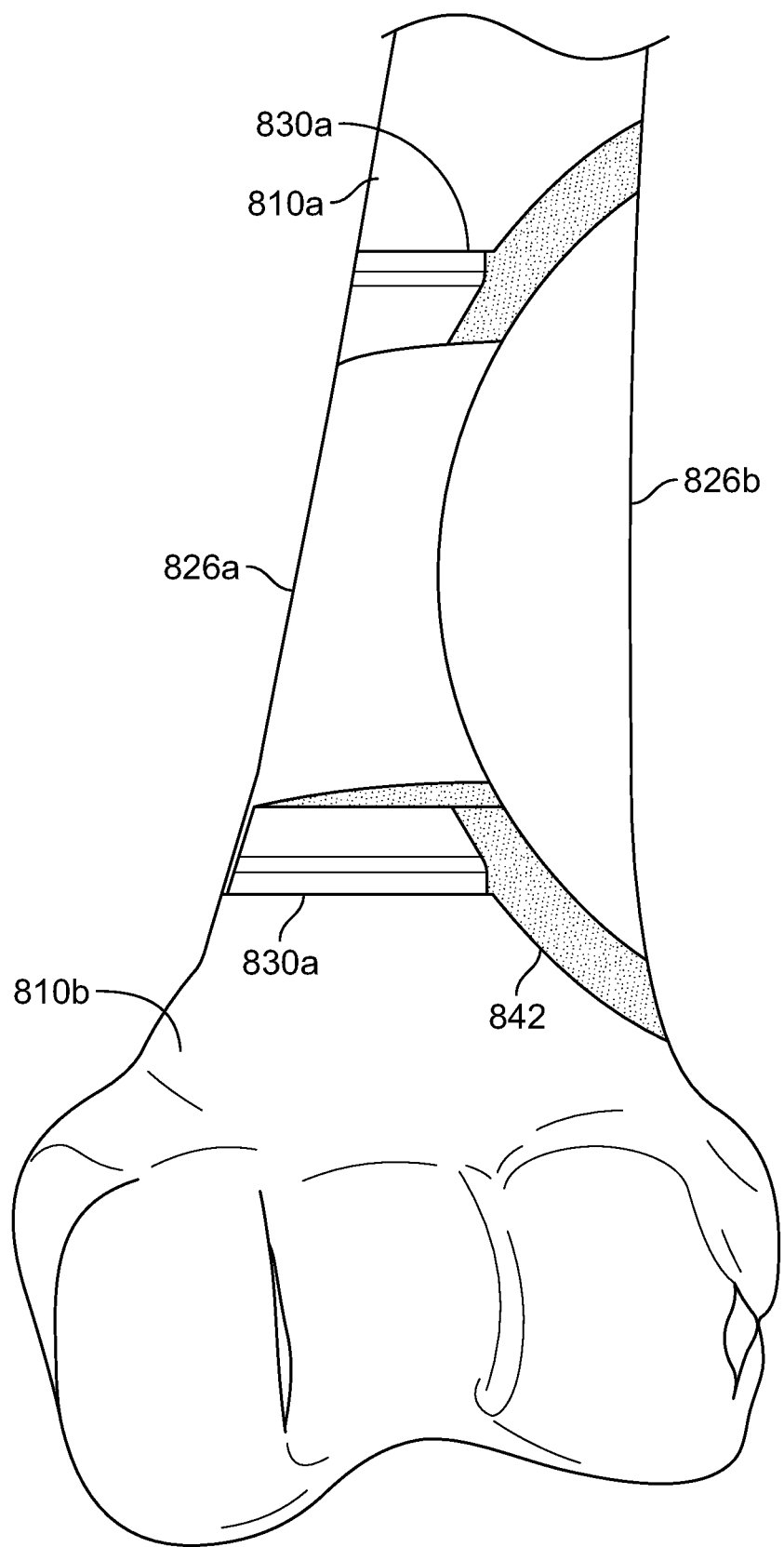
FIG. 12D illustrates the portions of the bone of FIG. 12C engaged with the implant components of FIG. 12A.

Turning to FIG. 12D, implant components 826a, 826b are engaged to one another and bone portion 810a, 810b to recreate the overall shape of a healthy bone. To engage implant components 826a, 826b as shown, first implant component 826a is first translated into engagement with bone portions 810a, 810b. Next, an end of rib 842 furthest from tabs 844 is inserted into either bone portion 810a, 810b (first bone portion 810a in the illustrated example) and second implant component 826b is rotated relative to first implant component 826a and bone portions 810a, 810b to drive rib 842 through channel 838 until tabs 844 abut a surface of first implant component 826a. Smaller channels, though not illustrated, are cut into bone to accommodate tabs 844.

Figure 13A:
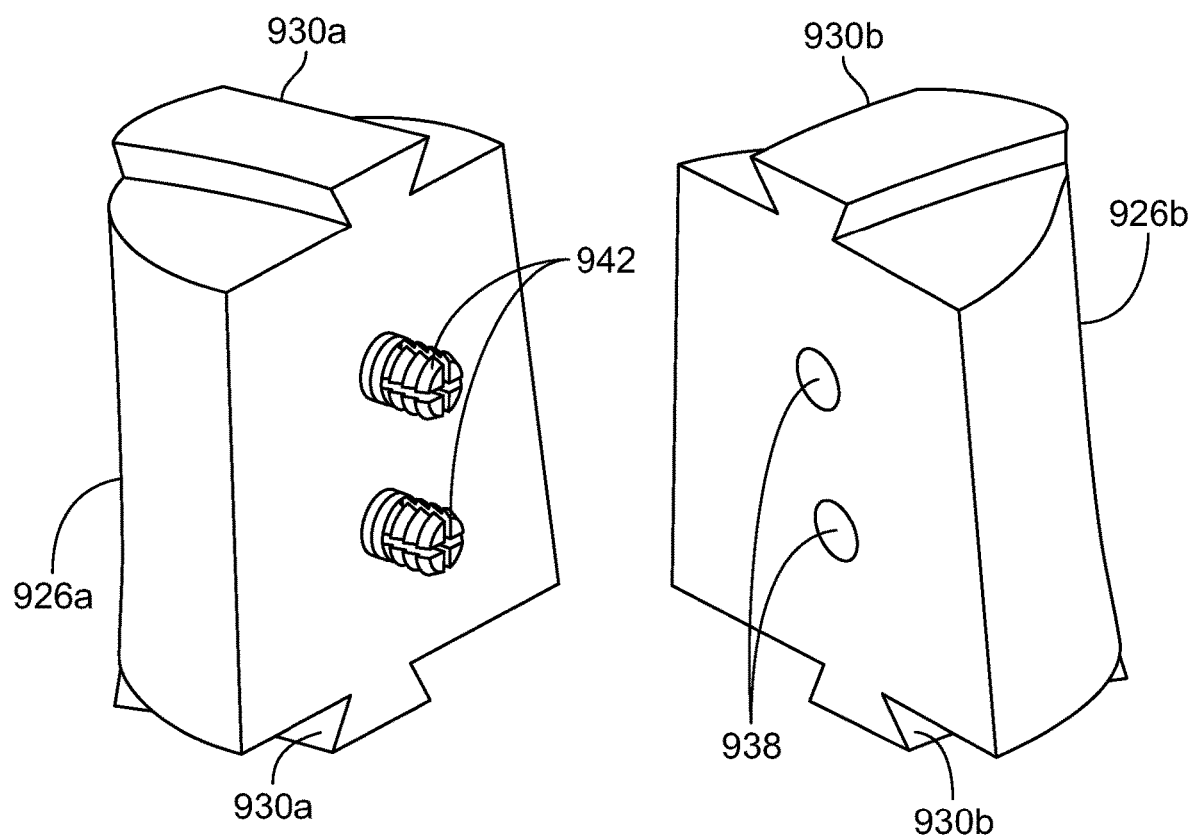
FIG. 13A illustrates a pair of interlocking implant components according to another example.

FIG. 13A illustrates implant components 926a, 926b according to another arrangement. A first implant component 926a includes two first rails 930a for engaging channels of corresponding shape cut into bone. The channels may be in the form of elongate grooves, notches, or tracks in the bone. The first implant component 926a also includes pegs 942a. The pegs 942a of the illustrated example are each provided by four resiliently flexible portions with external ridges. The external ridges have a sharp edge facing first implant component 926a and a tapered edge facing away from first implant component 926a, enabling pegs 942 to be inserted into corresponding holes and inhibiting pegs 942 from backing out of the corresponding holes. The first implant component 926a is provided with two first rails 930a and two pegs 942 in the illustrated example, but may be provided with other quantities of these features in other arrangements.

A second implant component 926b includes second rails 930b and apertures 938. The apertures 938 are each located to align with and dimensioned to receive, with an interference fit, a corresponding one of pegs 942.

The rails 930a, 930b are each shaped to have a dovetailing fit within a corresponding channel. In the illustrated example, rails 930a, 930b each have a trapezoidal cross-sectional shape, with rails 930a, 930b each being joined to the body of the corresponding implant component 926a, 926b at the narrower of the two parallel faces of the trapezoidal cross-section. However, in other arrangements, rails 930a, 930b may have any other cross-sectional shape that would have a dovetailing fit within a channel of the same cross-sectional shape.

Figure 13B:
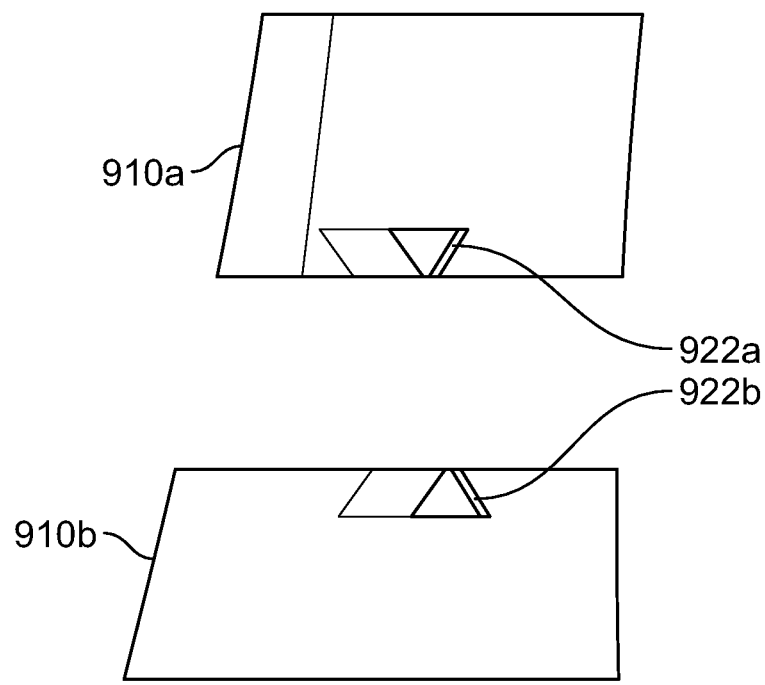
FIG. 13B is a translucent elevation view of two portions of a bone prepared to engaged the implant components of FIG. 13A.

Turning to FIG. 13B, a first bone portion 910a and a second bone portion 910b are prepared with a respective first channel 922a and second channel 922b having been cut therein. The first channel 922a and second channel 922b are each shaped to receive one of first rails 930a and one of second rails 930b. However, in other arrangements, each bone portion 910a, 910b may be provided with multiple, separate channels, each for receiving only one of first rail 930a or second rail 930b.

Figure 13C:
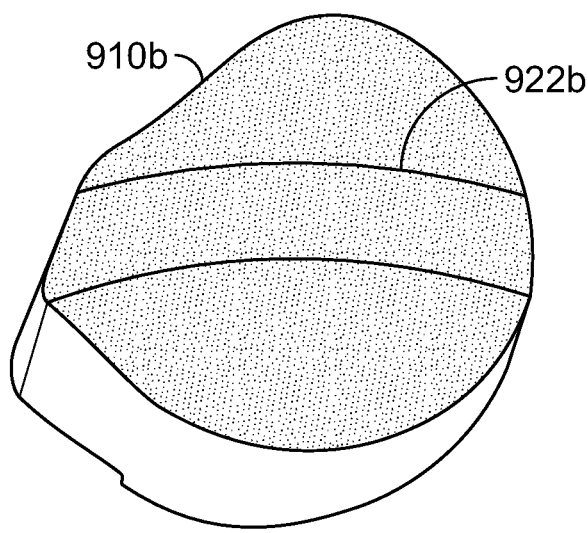
FIG. 13C is a top plan view of one of the portions of the bone of FIG. 13B.

Turning to FIG. 13C, second channel 922b extends along an asymmetrical curved centerline. Though not shown, first channel 922a extends along a similar curved centerline. The rails 930a, 930b each also extend along a centerline corresponding to a portion of the centerline of one of channels 922a, 922b, meaning they can be slotted into the corresponding portions of channels 922a, 922b from outside the bone. In other examples, channels 922a, 922b and rails 930a, 930b may be straight instead of curved, depending on the shape and location of the target bone portion to be removed, though asymmetric curvature such as that shown in FIG. 13C prevents implant components 926a, 926b, once engaged from one another, from moving relative to bone portions 910a, 910b.

Figure 13D:
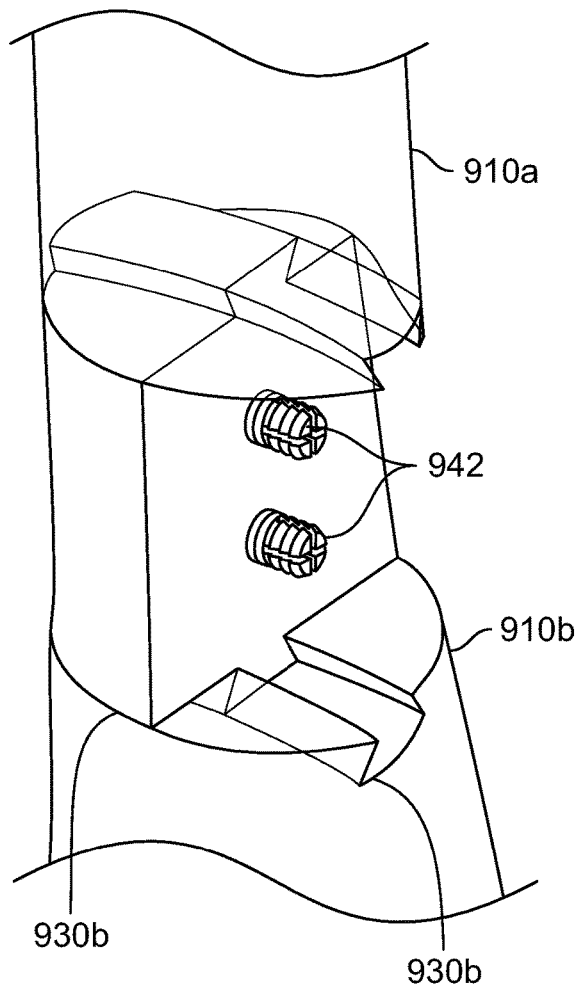
FIG. 13D is an oblique perspective view of one of the implant components of FIG. 13A engaged with the portions of the bone of FIG. 13B.

As shown in FIG. 13D, first implant portion 926a is slotted into engagement with first bone portion 910a and second bone portion 910b first, though second implant component 926b may be slotted into engagement first or simultaneously.

Figure 13E:
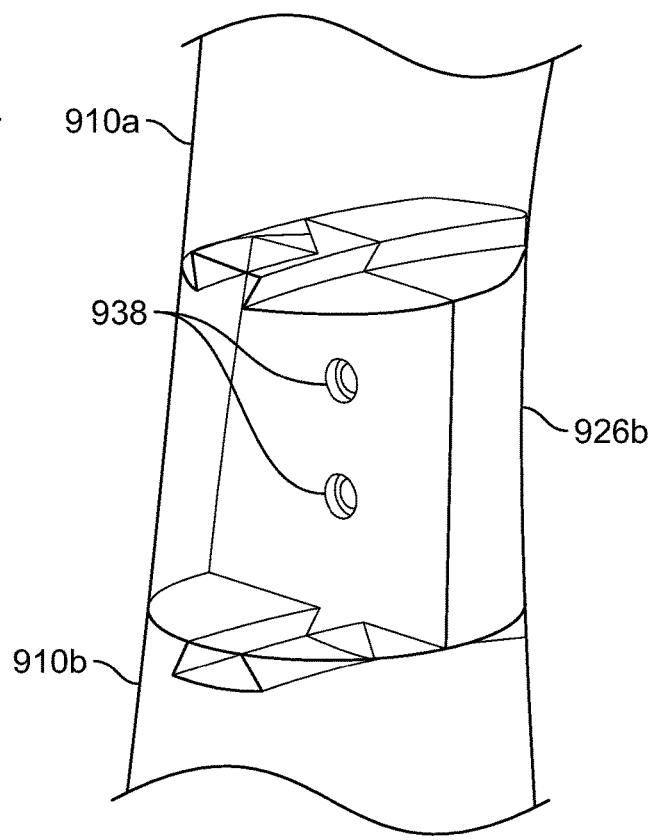
FIG. 13E is an oblique perspective view of both implant components of FIG. 13A engaged with each other and the portions of the bone of FIG. 13B, with one of the implant components being depicted as translucent.

When both implant components 926a, 926b are fully slotted into engagement with bone portions 910a, 910b as shown in FIG. 13E, pegs 942 (not visible in FIG. 13E) are received in apertures 938.

Figure 13G:
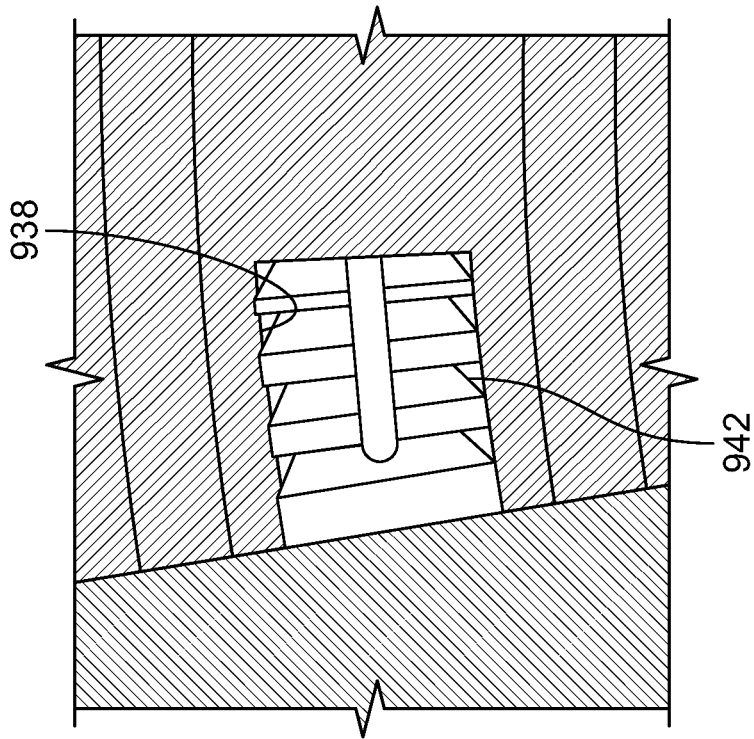
FIG. 13G is an enlarged portion of the cross-sectional view of FIG. 13F.
Figure 13F:
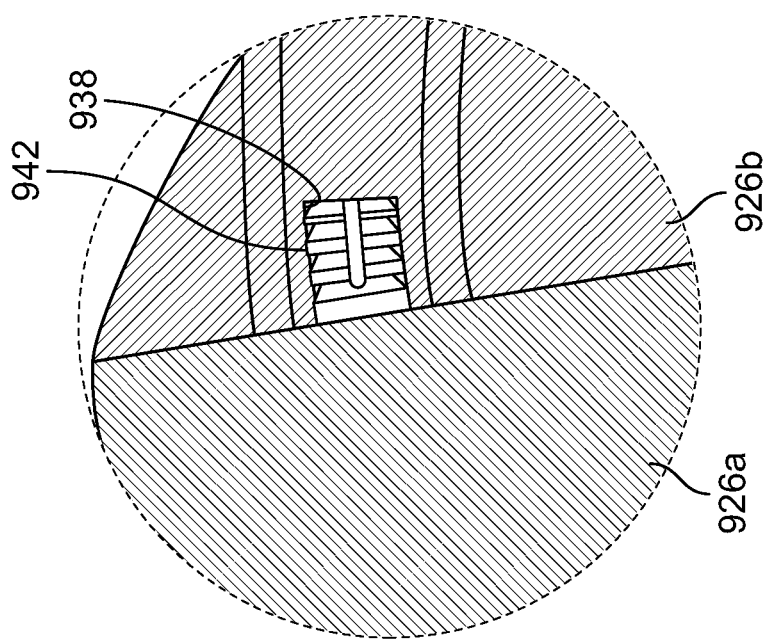
FIG. 13F is a cross-sectional view of the implant components of FIG. 13A in a mutually engaged configuration.

As shown in FIGS. 13F and 13G, the resiliently flexible elements forming pegs 942 expand outward to dig into internal surfaces of apertures 938 when pegs 942 are received in apertures 938. By digging into apertures 938, pegs 942 inhibit separation of implant components 926a, 926b after mutual engagement thereof, thus contributing to the stability of the body formed by implant components 926a, 926b within the bone.

Any of the above described implants, implant components, pins, or fasteners may be additively manufactured. Moreover, they may be manufactured, additively or otherwise, with porous features for promoting bone in-growth. The implants or implant components in particular may be manufactured to be slightly oversized for the removed portions of bone, or in some examples only for the channels engaged by the implants or implant components, to promote bone in-growth.

Although the concepts herein have been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. A method for treating bone, the method comprising:
   cutting away and removing a portion of a bone such that the bone is separated into two remaining bone portions;
   rejoining the two remaining bone portions with a patient-specific implant component;

securing the implant component to a first one of the remaining bone portions by disposing a pair of pins through the implant component and into the first one of the remaining bone portions such that the pair of pins engages one another within the first one of the remaining bone portions, wherein the pair of pins is a first pair of pins, and securing the implant component to a second one of the remaining bone portions by disposing a second pair of pins through the implant component and into the second one of the remaining bone portions such that the second pair of pins engages one another within the second one of the remaining bone portions, wherein the first pair of pins includes a first receiving pin including a neck portion and a first griping pin having two arms spaced to receive and grip the neck, and the second pair of pins includes a second receiving pin including a hole extending therethrough and a second gripping pin including two arms spaced to press against an interior of the hole of the second receiving pin when received therein.

2. The method of claim 1, comprising distracting the two remaining bone portions before disposing the implant component between the two remaining bone portions.

3. The method of claim 1, wherein the two arms of the first gripping pin are flexible.

4. The method of claim 1, wherein at least one of the two arms of the first gripping pin includes a rib.

5. The method of claim 1, wherein the first receiving pin includes a channel configured to receive the two arms of the first gripping pin.

6. The method of claim 1, wherein the step of securing the implant component to the first one of the remaining bone portions includes placing a first peg extending from the implant in a corresponding first hole of the first one of the remaining bone portions.

7. The method of claim 6, wherein the step of securing the implant component to the second one of the remaining bone portions includes placing a second peg extending from the implant in a corresponding second hole of the second one the remaining bone portions.

8. The method of claim 1, wherein the implant includes one or more apertures.

9. A method for treating bone, the method comprising:
cutting away and removing a portion of a bone such that the bone is separated into two remaining bone portions; and
rejoining the two remaining bone portions with a patient-specific implant component;
securing the implant component to a first one of the remaining bone portions by disposing a pair of pins through the implant component and into the first one of the remaining bone portions such that the pair of pins engages one another within the first one of the remaining bone portions, wherein the pair of pins is a first pair of pins, and
securing the implant component to a second one of the remaining bone portions by disposing a second pair of pins through the implant component and into the second one of the remaining bone portions such that the second pair of pins engages one another within the second one of the remaining bone portions,
wherein the first pair of pins includes a first receiving pin including a neck portion and a first griping pin having two arms spaced to receive and grip the neck.

10. The method of claim 9, wherein the second pair of pins includes a second receiving pin including a hole extending therethrough and a second gripping pin including two arms spaced to press against an interior of the hole of the second receiving pin when received therein.

11. The method of claim 9, wherein the step of securing the implant component to the first one of the remaining bone portions includes placing a first peg extending from the implant in a corresponding first hole of the first one of the remaining bone portions.

12. The method of claim 11, wherein the step of securing the implant component to the second one of the remaining bone portions includes placing a second peg extending from the implant in a corresponding second hole of the second one the remaining bone portions.

13. A method for treating bone, the method comprising:
cutting away and removing a portion of a bone such that the bone is separated into two remaining bone portions; and
rejoining the two remaining bone portions with a patient-specific implant component;
securing the implant component to a first one of the remaining bone portions by disposing a pair of pins through the implant component and into the first one of the remaining bone portions such that the pair of pins engages one another within the first one of the remaining bone portions, wherein the pair of pins is a first pair of pins, and
securing the implant component to a second one of the remaining bone portions by disposing a second pair of pins through the implant component and into the second one of the remaining bone portions such that the second pair of pins engages one another within the second one of the remaining bone portions,
wherein the second pair of pins includes a second receiving pin including a hole extending therethrough and a second gripping pin including two arms spaced to press against an interior of the hole of the second receiving pin when received therein.

14. The method of claim 13, wherein the first pair of pins includes a first receiving pin including a neck portion and a first griping pin having two arms spaced to receive and grip the neck.

15. The method of claim 13, wherein the step of securing the implant component to the first one of the remaining bone portions includes placing a first peg extending from the implant in a corresponding first hole of the first one of the remaining bone portions.

16. The method of claim 13, wherein the step of securing the implant component to the second one of the remaining bone portions includes placing a second peg extending from the implant in a corresponding second hole of the second one the remaining bone portions.

* * * * *